US006117658A

United States Patent [19]
Dennis et al.

[11] Patent Number: 6,117,658
[45] Date of Patent: Sep. 12, 2000

[54] METHODS OF MAKING POLYHYDROXYALKANOATES COMPRISING 4-HYDROXYBUTYRATE MONOMER UNITS

[75] Inventors: Douglas E. Dennis, Weyers Cave, Va.; Henry E. Valentin, Chesterfield, Mo.

[73] Assignee: James Madison University, Harrisonburg, Va.

[21] Appl. No.: 09/023,029

[22] Filed: Feb. 12, 1998

Related U.S. Application Data

[60] Provisional application No. 60/037,758, Feb. 13, 1997.

[51] Int. Cl.$^7$ ............................. C12P 7/62; C12P 7/52; C12P 7/42; C12P 1/04
[52] U.S. Cl. ................... 435/135; 435/141; 435/146; 435/170
[58] Field of Search .................. 435/135, 141, 435/146, 170

[56] References Cited

U.S. PATENT DOCUMENTS

| | | | |
|---|---|---|---|
| 4,477,654 | 10/1984 | Holmes et al. | 528/361 |
| 5,334,520 | 8/1994 | Dennis | 435/136 |
| 5,371,002 | 12/1994 | Dennis et al. | 435/142 |
| 5,512,456 | 4/1996 | Dennis | 435/69.1 |
| 5,518,907 | 5/1996 | Dennis | 435/141 |
| 5,569,595 | 10/1996 | Dennis | 435/135 |
| 5,750,848 | 5/1998 | Kruger et al. | 800/205 |
| 5,891,686 | 4/1999 | Dennis et al. | 435/135 |

FOREIGN PATENT DOCUMENTS

| | | |
|---|---|---|
| WO 91/00917 | 1/1991 | WIPO . |
| WO 95/05472 | 2/1995 | WIPO . |
| WO 95/21257 | 8/1995 | WIPO . |

OTHER PUBLICATIONS

Buckel et al., "Glutaconate CoA–Transferase from *Acidaminococcus fermentans*," *Eur. J. Biochem.* 118: 315–321, 1981.

Eikmanns and Buckel, "Properties of 5–Hydroxyvalerate CoA–Transferase from *Clostridium aminovalericum*," *Biol. Chem. Hoppe–Seyler* 371: 1077–1082, 1990.

Peoples and Sinskey, "Poly–β–hydroxybutyrate (PHB) Biosynthesis in *Alcaligenes eutrophus* H16," *The Journal of Biological Chemistry* 264(26): 15298–15303, 1989.

Priefert and Steinbüchel, "Identification and Molecular Characterization of the Acetyl Coenzyme A Synthetase Gene (acoE) of *Alcaligenes eutrophus*," *Journal of Bacteriology* 174(20): 6590–6599, 1992.

Scherf and Buckel, "Purification and Properties of 4–Hydroxybutyrate Coenzyme A Transferase from *Clostridium aminobutyricum*," *Applied and Environmental Microbiology* 57(9): 2699–2702, 1991.

Schweiger and Buckel, "On the dehydratioin of (R)–lactate in the fermentation of alanine to propionate by *Clostridium propionicum*," *FEBS* 171(1):79–84, 1984.

Söhling and Gottschalk, "Molecular Anlaysis of the Anaerobic Succinate Degradation Pathway in *Clostridium kluyveri*," *Journal of Bacteriology* 178(3): 871–880, 1996.

Söhling and Gottschalk, "Purification and characterization of a coenzyme–A–dependent succinate–semialdehyde dehydrogenase from *Clostridium kluyveri*," *Eur. J. Biochem.* 212: 121–127, 1993.

Valentin and Steinbüchel, "Application of enzymatically synthesized short–chain–length hydroxy fatty acid coenzyme A thioesters for assay of polyhydroxyalkanoic acid synthases," *Appl. Microbiol Biotechnol 40*: 699–709, 1994.

Valentin et al., "Metabolic pathway for biosynthesis of poly(3–hydroxybutyrate–co–4–hydroxybutyrate) from 4–hydroxybutyrate by *Alcaligenes eutrophus*," *Eur. J. Biochem.* 227: 43–60, 1995.

Steinbuchel et al., "Application of Recombinant Gene Technology for Production of Polyhydroxyalkanoic Acids: Biosynthesis of Poly(4–hydroxybutyric Acid) Homopolyester," J. Env. Pol. Deg., vol. 2, No. 2, 1994, pp. 67–74, 1994.

Saito et al., "Microbial synthesis and properties of poly(3–hydroxybutyrate–co–4–hydroxyburyrate) in *Comamonas acidovorans*," Int. J. Biol. Macromol., vol. 16, No. 2, 1994, pp. 99–104, 1994.

Kidwell et al., "Regulated Expression of the *Alcaligenes eutrophus* pha Biosynthesis Genes in *Escherichia coli*," Appl. Env. Microbiol., vol. 61, No. 4, Apr. 1995, pp. 1391–1398, Apr. 1995.

*Primary Examiner*—Robert A. Wax
*Attorney, Agent, or Firm*—Seed & Berry

[57] ABSTRACT

The PHA biosynthetic pathway is combined with a succinic semialdehyde metabolic pathway that metabolizes succinic semialdehyde via a 4-hydroxybutyryl-CoA intermediate in order to produce high levels of PHA comprising 4HB monomer units. This combination is particularly useful, in part, because the PHA biosynthetic pathway is well known and has been expressed to produce P(3HB) to levels as high as 70–80% of the cell dry weight, while the succinic semialdehyde metabolic pathway is also well known, and the combination of the two pathways means that production of PHAs comprising 4HB monomer units does not depend on immediate precursors of 4-hydroxybutyrate. Rather, the production of the PHAs comprising 4HB monomer units can occur simply from the extraction of succinate or succinyl-CoA from the citric acid cycle when the host cell is grown on an inexpensive carbon source such as glucose.

67 Claims, 2 Drawing Sheets

METHODS OF MAKING POLYHYDROXYALKANOATES COMPRISING 4-HYDROXYBUTYRATE MONOMER UNITS

CROSS-REFERENCE TO RELATED APPLICATION

This application claims the benefit of U.S. Provisional Application No. 60/037,758, filed Feb. 13, 1997.

TECHNICAL FIELD

The present invention relates generally to the production of poly-β-hydroxyalkanoates ("PHAs") comprising 4-hydroxybutyrate monomer units, including the production of poly(3-hydroxybutyrate-co-4-hydroxybutyrate) ("P(3HB-co-4HB)") and poly(4-hydroxybutyrate) ("P(4HB)"), and to associated methods, vectors, host cells and compositions concerning the same.

BACKGROUND OF THE INVENTION

Poly-β-hydroxyalkanoates (PHAs) are bacterial storage polymers that are synthesized by bacteria when carbon source levels are high and other nutritional necessities, such as nitrogen, phosphate, oxygen, or sulfur, are limited (Anderson, A. J., E. A. Dawes, *Microbiol. Rev.* 54:450–472, 1990; Steinbüchel, A., H. G. Schlegel, *Mol. Microbiol.* 5:535–542, 1991). The first PHAs that were identified consisted of saturated 3-hydroxy fatty acids, but more recently identified polymers have been shown to contain double bonds (Huijberts, G. N. et al., *Appl. and Environ. Microbiol.* 58:536–544, 1992; Lageveen, R. G. et al., *Appl. and Environ. Microbiol.* 54:2924–2932, 1988).

General formulas for PHA polymers include the following:

where the R group can range from a single methyl group (to provide a 3-hydroxybutyrate subunit) up to about a 13-carbon chain (to provide 3-hydroxyhexadecanoate). In addition, the R group may simply be a hydrogen (to provide 3-hydroxypropionate). In an alternative form, the PHA can have a 4-hydroxybutyrate monomer unit ("4HB") of the following general formula:

PHAs that consist essentially of, or are homogeneous for, 4HB monomer units are known as poly(4-hydroxybutyrate). PHAs comprising both 3-hydroxybutyrate monomer units and 4-hydroxybutyrate monomer units are known as poly (3-hydroxybutyrate-co-4-hydroxybutyrate). PHAs comprising 4HB are recently discovered and have attracted considerable interest because of their superior qualities for certain plastic applications. For example, P(3HB-co-4HB) has increased flexibility in thermoplastic uses (Kunioka et al., *Appl. Microbiol Biotechnol.* 30:569–573, 1989; Doi, Y., et al., *Macromolecules* 23:26–31, 1990; Doi, Y., et al., *Int. J. Biol. Macromol.* 12:101–106, 1990; Saito and Doi, *Int. J. Biol. Macromol.* 16:99–104, 1994).

PHAs have been synthesized by the action of three enzymes: β-ketothiolase ("3-ketothiolase"), acetoacetyl-CoA reductase ("reductase"), and poly-β-hydroxyalkanoate synthase ("PHA synthase") (see, e.g., Oeding and Schlegel, *Biochem. J.* 134:239, 1973; Senior and Dawes, *Biochem. J.* 134:225, 1973). These enzymes are encoded by genes known as phaA, phaB and phaC, respectively, and are known as the "polyhydroxyalkanoate biosynthetic pathway" (or "PHA biosynthetic pathway"). For example, in the production of poly-3-hydroxybutyrate ("P(3HB)") in *Ralstonia eutropha*, 3-ketothiolase condenses two acetyl-CoA molecules to acetoacetyl-CoA reductase (*Ralstonia eutropha* was formerly known as *Alcaligenes eutropha* (Yabuuchi, E. et al., *Microbiol. Immunol.* 39:897–904, 1995)). Acetoacetyl-CoA reductase reduces this compound to 3-hydroxybutyryl-CoA. PHA synthase then polymerizes 3-hydroxybutyryl-CoA into PHB. Other PHAs, including medium chain and long chain PHAs, are produced under other conditions, which can include pathways comprising enzymes other than phaA and/or phaB.

P(3HB-co-4HB) has been produced from the above pathway by feeding expensive precursors such as 4-hydroxybutyrate, 1,4-butanediol or 4-butyrolactone to wild type or mutant strains of *Ralstonia eutropha*. Normally the molar levels of 4HB in the copolymer are relatively low, but γ-butyrolactone has reportedly been fed to *Alcaligenes latus* to obtain P(3HB-co-4HB) levels that are approximately 60% of the cell dry weight and which contain 7–12 mol % 4-hydroxybutyrate (4HB) monomers (Soejima and Doi, *International Symposium on Bacteriol Polyhydroxyalkanoates*, Davos, Switz., 1996).

Steinbüchel et al., *J. Env. Pol. Deg.* 2, 67–74, 1994, have isolated *A. eutrophus* mutants that were able to accumulate a P(4HB) homopolyester. When these mutants were supplemented with the *A. eutrophus* PHA synthase gene, P(4HB) homopolyester was accumulated to levels of approximately 30% of the cell dry weight.

The field of PHA production has altered its focus in recent years to include plant produced PHAs (Eschenlauer, A. C. et al., *Abstr. Annul. Meet. International Symposium on Bacterial Polyhydroxyalkanoates*, Montreal, Canada, 85:66, 1994; Hahn, J. J., *Abstr. Annu. Meet. International Symposium on Bacterial Polyhydroxyalkanoates*, Montreal, Canada, 82:65; Landschulze, V. et al., *Abstr. Annu. Meet. International Symposium on Bacterial PHA*, Montreal, Canada, 86:66; Nawrath, C. et al., *Abstr. Annu. Meet. International Symposium on Bacterial Polyhydroxyalkanoates*, Montreal, Canada, 83, 1994; Nawrath, C., *Proc. Natl. Acad. Sci.* 91:12760–64, 1994; Poirier, Y., *Adv. Mater.* 5:30–36, 1993; Pool, R., *Science* 245:1187–1189, 1989; Poirier, Y., *Sci.* 256:520–523, 1992). Such technology includes the expression of the *A. eutrophus* pha synthesis genes in *Arabidopsis thaliana* (Poirier, Y., *Sci.* 256:520–523, 1992) with the formation of PHA reaching 14% of the dry weight of the leaves (Nawrath, C., et al., *Proc. Nat. Acad. Sci. USA* 91:12760–12764). PHA production in plants may be less expensive than PHA production in bacteria.

Further information with respect to the production of PHAs can be found in U.S. Pat. Nos. 5,334,520, 5,371,002, 5,512,456, and 5,569,595, and in PCT applications PCT/US93/05187, PCT/US94/03252, PCT/US95/01433, and PCT/US95/01471, as well as in Kidwell, J., Valentin, H. E., and Dennis, D., *Appl. Environ. Microbiol.* 61:1391–1398, 1995), Huisman, G. W., et al., Genetic Analysis Of Polyester Synthesis, p. 451–452, in E. A. Dawes (Herausg.), Novel Biodegradable Microbial Polymers, Kluwer Academic Publishers, Netherlands, 1990; Slater, S., et al., *Appl. Microbiol.* 58:1089–1094, 1992.

A disadvantage with present production systems for PHA comprising 4HB monomer units is that they are too expensive for practical application, for example, because of the high-cost carbon substrates that are precursors of 4HB monomer units found in PHA. Conversely, the less expensive P(3HB) is brittle, and thus not usable for many applications, while polymers comprising significant amounts of polyhydroxyoctanoate (and/or longer chain subunits) are too flexible for many plastic uses, and thus similarly unsuitable for many applications. PHA comprising 4HB monomer units would provide many useful plastic properties not found in other PHAs (Saito, Y. et al., *Int. J. Biol. Macromol.* 16:99–104, 1994).

Thus, there is a need in the art for methods and constructs capable of producing PHA comprising 4HB monomer units in large amounts in an efficient, economic manner. The present invention fulfills this need and provides other related advantages.

SUMMARY OF THE INVENTION

In brief, the present invention provides constructs and methods for the production of PHA comprising 4HB monomer units, thereby providing biodegradable plastics having superior properties.

In one aspect the present invention provides a process for producing a polyhydroxyalkanoate comprising a 4-hydroxybutyrate monomer units, the method comprising: providing a host cell containing at least one recombinant sequence that encodes a polyhydroxyalkanoate biosynthetic pathway, and at least one recombinant sequence that encodes a succinic semialdehyde metabolic pathway that metabolizes succinic semialdehyde via a 4-hydroxybutyryl-CoA intermediate; and, cultivating the host cell under suitable conditions to obtain expression of both the polyhydroxyalkanoate biosynthetic pathway and the succinic semialdehyde metabolic pathway within the host cell, to produce the polyhydroxyalkanoate. This and other aspects and embodiments of the invention have various general or preferred embodiments and/or sub-embodiments, and therefore discussion of an embodiment as preferred for one aspect of the invention indicates that it is also preferred for other aspects or embodiments of the invention, unless indicated otherwise.

In one preferred embodiment, the recombinant sequences are contained on one or more vector constructs. In another preferred embodiment, the method further comprises the step of isolating the polyhydroxyalkanoate from the host cell. In a further preferred embodiment, the at least one sequence encoding the succinic semialdehyde metabolic pathway further comprises a sequence encoding a succinic semialdehyde dehydrogenase, which preferably is a succinic semialdehyde dehydrogenase is able to convert succinyl-CoA to succinic semialdehyde. In yet another preferred embodiment, the at least one sequence encoding the succinic semialdehyde metabolic pathway further comprises a sequence encoding a succinyl-CoA:CoA transferase.

In still another preferred embodiment, the polyhydroxyalkanoate biosynthetic pathway is encoded by a single sequence contained in a first vector construct, and the succinic semialdehyde metabolic pathway is encoded by a single sequence contained in a second vector construct. Alternatively, the polyhydroxyalkanoate biosynthetic pathway and the succinic semialdehyde metabolic pathway are encoded by sequences contained in a single vector construct.

The present invention provides preferred sources and host cells, which are discussed in further detail in the Detailed Description of the Invention, below, and that include the following. The succinic semialdehyde metabolic pathway can be from *Clostridium kluyveri*, while the polyhydroxyalkanoate biosynthetic pathway can be from *Ralstonia eutropha* and the polyhydroxyalkanoate synthase from *Nocardia corallina*. Preferrred host cells include *Escherichia coli*, Klebsiella, particularly *Klebsiella aerogenes* and *Klebsiella oxytoca*, plant host cells, insect host cells and spider host cells. In one preferred embodiment, the host cell has an inhibiting mutation in its CoA-independent NAD-dependent and/or NADP-dependent succinic semialdehyde dehydrogenase.

In another preferred embodiment, the step of cultivating comprises cultivating the host cell on a carbon source that does not contain a structurally related precursor of 4-hydroxybutyrate, for example 4-hydroxybutyrate, 1,4-butanediol or 4-butyrolactone. Alternatively, the step of cultivating comprises cultivating the host cell on a carbon source comprising a sugar having a 5-carbon or 6-carbon ring, for example glucose, sucrose, fructose or lactose.

In another aspect, the present invention provides a process for producing polyhydroxyalkanoate comprising 4-hydroxybutyrate monomer units, the method comprising: providing a host cell able to synthesize poly-β-hydroxyalkanoate via a polyhydroxyalkanoate biosynthetic pathway, the host cell containing at least one recombinant sequence that encodes a succinic semialdehyde metabolic pathway that metabolizes succinic semialdehyde via a 4-hydroxybutyryl-CoA intermediate; and, cultivating the host cell under suitable conditions to obtain expression of the poly-β-hydroxyalkanoate pathway and the succinic semialdehyde metabolic pathway in the host cell, to produce the polyhydroxalkanoate.

In a further aspect, the present invention provides a process for producing a polyhydroxyalkanoate comprising 4-hydroxybutyrate monomer units, the method comprising: providing a host cell that metabolizes succinic semialdehyde via a succinic semialdehyde metabolic pathway that uses a 4-hydroxybutyryl-CoA intermediate, the host cell containing at least one recombinant sequence that encodes a polyhydroxyalkanoate biosynthetic pathway; cultivating the host cell under suitable conditions to obtain expression of the succinic semialdehyde metabolic pathway and the polyhydroxyalkanoate biosynthetic pathway in the host cell, to produce the polyhydroxyalkanoate. In a preferred embodiment, the polyhydroxyalkanoate is poly(4-hydroxybutyrate) and wherein the polyhydroxyalkanoate biosynthetic pathway consists of a polyhydroxyalkanoate synthase.

In still a further aspect, the present invention provides a host cell containing at least one recombinant sequence that encodes a polyhydroxyalkanoate biosynthetic pathway, and at least one recombinant sequence that encodes a succinic semialdehyde metabolic pathway that metabolizes succinic semialdehyde via a 4-hydroxybutyryl-CoA intermediate. Preferably, one or both of the recombinant sequences are contained in one or more vector constructs that express the sequences.

In yet another aspect, the present invention provides a transgenic plant whose germ or somatic cells contain at least one recombinant sequence that encodes a polyhydroxyalkanoate biosynthetic pathway, and at least one sequence that encodes a succinic semialdehyde metabolic pathway that metabolizes succinic semialdehyde via a 4-hydroxybutyryl-CoA intermediate. In a preferred embodiment, the plant is *Arabidopsis thaliana*. In another preferred embodiment, the polyhydroxyalkanoate biosynthetic pathway comprises a polyhydroxyalkanoate synthase from *Nocardia corallina pha* operably linked to a promoter such that the gene is able to be expressed in the transgenic plant.

In still yet another aspect, the present invention provides a polyhydroxyalkanoate comprising 4-hydroxybutyrate monomer units produced according to the method described herein. The present invention also provides polyhydroxyalkanoate comprising 4-hydroxybutyrate monomer units and having a molecular weight that is greater than about 600,000 daltons, typically greater than about 800,000 daltons, preferably greater than about 1,000,000 daltons and further preferably greater than about 1.2, 1.5 or 2.0 million daltons, and a polydispersity that is generally less than about 2, typically less than about 1.6, preferably less than about 1.5, and further preferably less than about 1.4 or 1.3.

In still yet a further aspect, the present invention provides a vector construct that expresses at least one sequence that encodes a polyhydroxyalkanoate biosynthetic pathway, and at least one sequence that encodes a succinic semialdehyde metabolic pathway. Such vector constructs can also encode one or more of the other genes discussed herein.

These and other aspects of the present invention will become evident upon reference to the following detailed description and attached drawings.

Various references are set forth herein (both above and below) that describe in more detail certain procedures or compositions (e.g., plasmids, etc.); all such references are incorporated herein by reference in their entirety.

DETAILED DESCRIPTION OF THE INVENTION

PHAs comprising 4HB monomer units are PHA plastics having superior qualities for certain uses (Saito, Y. et al., Int. J. Biol. Macromol. 16:99–104, 1994). In the past, PHAs comprising 4HB monomer units have been produced by feeding expensive precursors such as 4-hydroxybutyrate, 1,4-butanediol or 4-butyrolactone to wild type or mutant strains of bacteria such as *Ralstonia eutropha* and *Alcaligenes latus*. The present invention discloses methods of producing PHAs comprising 4HB monomer units using much less expensive substrates such as glucose, sucrose and fructose. Additionally, the PHAs comprising 4HB monomer units can be produced in host cells other than *Ralstonia eutropha* and *Alcaligenes latus*. Such preferred host cells include superior bacteria such as *E. coli* and Klebsiella, as well as plants and even insect or spider host cells (plant, insect and spider cells can permit the PHAs comprising 4HB monomer units to be produced in combination with other desirable polymers, such as cotton and silk).

The present invention combines the PHA biosynthetic pathway with a succinic semialdehyde metabolic pathway that metabolizes succinic semialdehyde via a 4-hydroxybutyryl-CoA intermediate in order to produce PHA comprising high levels of 4HB monomer units. This combination is particularly useful, in part, because the PHA biosynthetic pathway is well known and has been expressed to produce P(3HB) to levels as high as 70–80% of the cell dry weight (Schubert, P. A., et al., *J. Bact.* 170:5837, 1988; Slater, S. C., et al., *J. Bact.* 170:4431, 1988; Peoples and Sinskey, *J. Biol. Chem.* 264:15298, 1989; PCT/US95/01433; PCT/US95/01471), while the succinic semialdehyde metabolic pathway is also well known, and the combination of the two pathways means that production of PHAs comprising 4HB monomer units does not depend on immediate precursors of 4-hydroxybutyrate. Rather, the production of the PHAs comprising 4HB monomer units can occur simply from the extraction of succinate or succinyl-CoA from the citric acid cycle when the host cell is grown on an inexpensive carbon source such as glucose, sucrose, fructose or lactose. Such production can also occur from other metabolic pathways that provide succinic semialdehyde.

Thus, in order to economically, efficiently produce PHA comprising 4HB monomer units, in one aspect the present invention provides a host cell that contains a recombinant PHA biosynthetic pathway and a recombinant succinic semialdehyde metabolic pathway that metabolizes succinic semialdehyde via a 4-hydroxybutyryl-CoA intermediate. In alternative aspects, the present invention provides a recombinant PHA biosynthetic pathway or a recombinant succinic semialdehyde metabolic pathway contained in a host cell that non-recombinantly contains the corresponding pathway (e.g., if the host cell contains a non-recombinant PHA biosynthetic pathway then a recombinant succinic semialdehyde metabolic pathway is provided to the cell, and vice-versa).

Providing one or both of the pathways in recombinant form, which means a form wherein the encoding sequences have been excised from their native genome, yields many significant advantages. For example, the amount of expression and the timing of the expression of the pathways can be carefully controlled. Additionally, a host cell (which is a cell that contains the recombinant sequences) can be chosen that is superior for PHA production because the host cell has no PHA degradation enzymes or because the host cell can be grown highly economically and in large quantities. These advantages due to recombinant production of PHA comprising 4HB monomer units are unexpected, in part, because the interplay between the PHA biosynthetic pathway and the succinic semialdehyde metabolic pathway, and therefore their combination, was not understood before the present invention. In order to attain these ends, the present invention also provides vector constructs capable of expressing either or both of the PHA biosynthetic pathway and the recombinant succinic semialdehyde metabolic pathway, including regulating the transcription and/or translation of such pathways. The present invention also provides methods of using such constructs to produce PHAs, host cells transformed with such constructs, and PHAs produced according to the methods of the present invention.

As used herein, "PHA biosynthetic pathway" comprises a PHA synthase (encoded by the phaC gene: "PHA synthase" has also been called "PHA polymerase" and as used herein, unless otherwise indicated, includes both PHA synthesis and PHB synthesis). Preferably, the PHA biosynthetic pathway also comprises a 3-ketothiolase (encoded by the phaA gene) and/or an acetoacetyl-CoA reductase (encoded by the phaB gene). Each of these proteins, and their encoding genes, is well known. (Oeding and Schlegel, *Biochem. J.* 134:239, 1973: Senior and Dawes, *Biochem. J.* 134:225, 1973.) For example, the PHA biosynthetic pathway of *Ralstonia eutropha* H16 has been cloned into *Escherichia coli* (Slater et al., *J. Bact.* 170:4431, 1988; Schubert et al., *J. Bact.* 170:5837, 1988) and the DNA sequence of the pathway has been determined (Peoples and Sinskey, *J. Biol. Chem.* 264:15293, 1989; Peoples and Sinskey, *J. Biol. Chem.* 264:15298, 1989; Janes et al., *Novel Biodegradable Microbial Polymers*, 175, 1990). The genes are located in the pha operon in the order phaC, phaA and phaB. The transcriptional start site has been determined by deletion analysis (Janes et al., supra) and by S1 nuclease mapping (Schubert et al., *J. Bact.* 173:168, 1991). The promoter for the PHA operon is very similar to the *E. coli* promoter recognized by σ70 (Rosenberg and Court, *Ann. Rev. Genet.* 13:319, 1979), and the phb operon is transcribed in *E. coli*. The transcriptional start site is located approximately 300 bp upstream from the start of the phaC translational start site.

Clones that carry the PHA operon on a multicopy plasmid can produce PHAs to levels as high as 80% of cell weight in media containing whey, a waste product of cheese production that contains a high concentration of lactose (Janes et al., supra). The use of whey, and other low-cost food sources such as sucrose-containing food sources, has been a major stride in decreasing the overall cost of industrial scale production of PHAs. Another significant expense in the industrial production of PHAs is the inclusion of an antibiotic in the growth culture of bacteria useful for PHA production. For example, in a 100,000 liter fermentor, the cost of producing about 22,000 pounds of PHB (which would be about $22,000 if no antibiotic were necessary) is increased by over $14,000 when the commonly used antibiotic chloramphenicol is added to the mixture.

Further information with respect to the production of PHAs can be found in U.S. Pat. Nos. 5,334,520, 5,371,002, 5,512,456, and 5,569,595, and in PCT applications PCT/US93/05187, PCT/US94/03252, PCT/US95/01433, and PCT/US95/01471, as well as in Kidwell, J., Valentin, H. E., and Dennis, D., *Appl. Environ. Microbiol.* 61:1391–1398, 1995), Huisman, G. W., et al., Genetic Analysis Of Polyester Synthesis, p. 451–452, in E. A. Dawes (Herausg.) Novel Biodegradable Microbial Polymers, Kluwer Academic Publishers, Netherlands, 1990; Slater, S., et al., *Appl. Microbiol.* 58:1089–1094, 1992.

Figure 1:
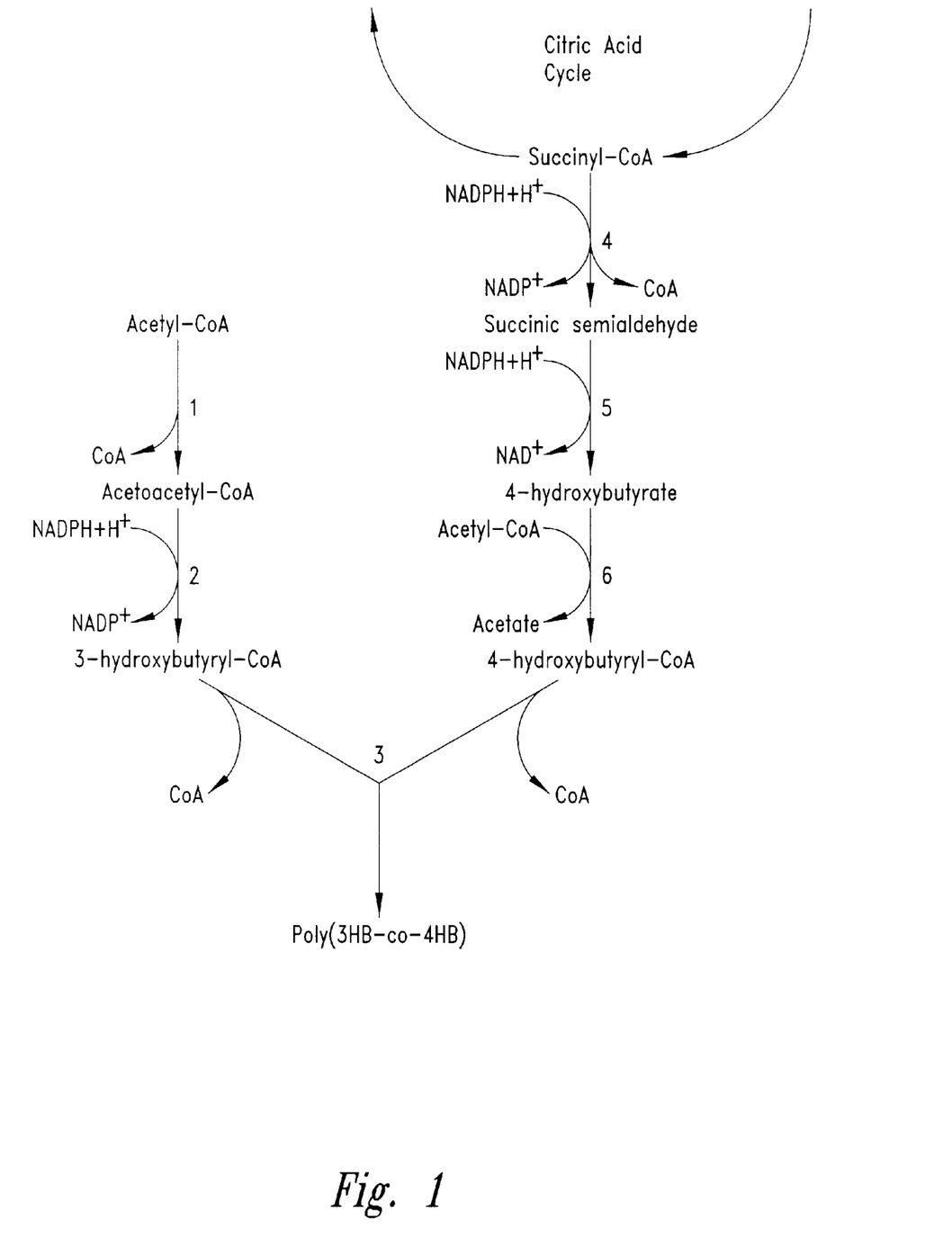
FIG. 1 depicts a proposed pathway for P(3HB-co-4HB) synthesis in recombinant *E. coli* harboring plasmids carrying the PHA synthesis operon from *A. eutrophus* and the succinate utilization pathway from *C. kluyveri*. The enzymes are as follows: 1: 3-ketothiolase; 2: acetoacetyl-CoA reductase; 3: PHA synthase; 4: succinic semialdehyde dehydrogenase; 5: 4-hydroxybutyrate dehydrogenase; and, 6: acetyl-CoA:4-hydroxybutyrate-CoA transferase.

FIG. 1 sets forth an exemplary mode of action of the 3-ketothiolase, acetoacetyl-CoA reductase, and PHA synthase as they interact with the succinic semialdehyde metabolic pathway to produce PHA comprising 4HB monomer units (the succinic semialdehyde metabolic pathway is discussed further below). Briefly, 3-ketothiolase (1) condenses two acetyl-CoA molecules to acetoacetyl-CoA reductase. Acetoacetyl-CoA reductase (2) reduces acetoacetyl-CoA reductase to 3-hydroxybutyryl-CoA. PHA synthase (3) then polymerizes 3-hydroxybutyryl-CoA into PHA comprising 4HB monomer units, for example. In an alternative embodiment that is preferred for the production of P(4HB) homopolymer, the PHA biosynthetic pathway comprises only a functional PHA synthase, which polymerizes 4-hydroxybutyryl-CoA into P(4HB). The use of a PHA biosynthetic pathway comprising only the PHA synthase can also give rise to production of PHA comprising 4HB monomer units if 4-hydroxybutyryl-CoA and/or other 3-hydroxyacyl-CoAs (or other suitable activated substrates) are provided by alternative pathways, in which they may be intermediates.

In a preferred embodiment, the 3-ketothiolase, the acetoacetyl-CoA reductase and the PHA synthase are all from *Ralstonia eutropha*. Alternatively, one, two or all of the 3-ketothiolase, acetoacetyl-CoA reductase or PHA synthase is obtained from Azotobacter, Beijerinckia, Pseudomonas, Rhizobium, Rhodospirillum, *Azotobacter beijerinckii, Nocardia corallina, C. violaceum, C. testosteroni, C. terrigena*, Vibrio, Acinetobacter, or Zooglea. Exemplary bacteria for 3-ketothiolases include: *Zooglea ramigera, Rhizobium meliloti, Paracoccus denitrificans, Thiocystis violacea, Chromatium vinosum*, and Acinetobacter sp. Exemplary bacteria for reductases include: *Zooglea ramigera, Rhizobium meliloti, Paracoccus denitrificans, Chromatium vinosum*, and Acinetobacter sp. Exemplary bacteria for PHA synthases include: *Thiocystis violacea, Thiocapsa pfennigii, Chromatium vinosum, Pseudomonas aeruginosa, Pseudomonas oleovorans, Pseudomonas putida, Pseudomonas fluoroscens, Nocardia corallina, Rhodococcus ruber, Rhodobacter sphaeroides, Paracoccus denitrificans, Rhizobium meliloti*, Acinetobacter sp., *Methylobacterium extorquens*, Vibrio sp., *Chromobacterium violaceum, Comomonas testosteroni, V. parahemolyticus, Comomonas verrigena* and *Aeromonas caviae*. The 3-ketothiolase, acetoacetyl-CoA reductase and PHA synthase need not all be from the same organism. For example, 3-ketothiolase and acetoacetyl-CoA reductase may both be from *Ralstonia eutropha*, while the PHA synthase can be from *Nocardia corallina*. The *N. corallina* synthase is preferred for certain embodiments of the present invention because it permits the production of PHAs comprising copolymers or terpolymers comprising $C_4$ and $C_6$ or $C_5$ and $C_7$ subunits (Dennis, D. *Proc. Int'l. Symp. Bact. on Polyhydroxyalkolates*, McGill Univ., Montreal, Canada, 1994). Such plastics are biodegradable and non-brittle.

Turning to the succinic semialdehyde metabolic pathway, it is typically found as a part of the succinyl-CoA metabolic pathway (see Söhling and Gottschalk, *J. Bact.* 178:871–880, 1996; Hardman, J. K. et al., *J. Biol. Chem.* 238:2081–2087, 1963; Hardmann, J. K. et al., *J. Biol. Chem.* 238:2088–2093, 1963). In a preferred embodiment, the term "succinic semialdehyde metabolic pathway" as used herein preferably includes the full succinyl-CoA metabolic pathway. However, PHA comprising 4HB monomer units can be produced utilizing cellular pathways other than the full succinyl-CoA metabolic pathway, as long as the pathway produces a succinic semialdehyde, and therefore the full succinyl-CoA metabolic pathway is not necessary to carry out the invention.

FIG. 1 depicts the succinyl-CoA metabolic pathway as it interacts with the PHA biosynthetic pathway. The succinyl-CoA metabolic pathway begins by reducing succinyl-CoA to succinic semialdehyde and CoA by the action of a succinic semialdehyde dehydrogenase (4). One example of such succinic semialdehyde dehydrogenase is encoded by the sucD gene of *Clostridium kluyveri* (Söhling and Gottschalk, *J. Bact.* 178:871–880, 1996). In a lesser preferred embodiment, the present invention uses a different type of succinic semialdehyde dehydrogenase that may convert succinate to succinic semialdehyde. This type of enzyme is referred to herein as a CoA-independent NAD-dependent or NADP-dependent succinic semialdehyde dehydrogenase (Valentin et al., *Eur. J. Biochemistry* 227:43–60, 1995). Still other pathways can also provide a succinic semialdehyde suitable for use in the present invention.

In a preferred embodiment, the host cell has an inhibiting (i.e., down-regulating), and preferably inactivating, mutation in the CoA-independent NAD-dependent succinic independent semialdehyde dehydrogenase and/or CoA-independent NADP-dependent succinic semialdehyde dehydrogenase. As noted above, these enzymes are capable of metabolizing succinic semialdehyde to succinate, thereby interfering with the action of the succinic semialdehyde metabolic pathway of the present invention.

Once the succinic semialdehyde has been obtained, the succinic semialdehyde metabolic pathway begins to work. Succinic semialdehyde is reduced to 4-hydroxybutyrate ("4HB") by the action of a 4-hydroxybutyrate dehydrogenase (5) (such as that encoded by the 4hbD gene of *Clostridium kluyveri* or the gbd gene from *R. eutropha* (Valentin, H. E., et al., *Eur. J. Biochem.* 227:43–60, 1995)). 4HB is then activated to a 4-hydroxybutyryl-CoA intermediate by a CoA transferase (such as the acetyl-CoA:4-hydroxybutyrate CoA transferase (orfZ) from *C. kluyveri* and/or a short chain fatty acid acyl-CoA synthetase). Preferably, the short chain fatty acid acyl-CoA synthetase has a specificity for fatty acids having a C3 to C7 backbone. Finally, as noted above, the 4-hydroxybutyryl-CoA is converted to PHA comprising 4HB monomer units by a PHA synthase (3).

In a preferred embodiment, the genes for the succinyl-CoA metabolic pathway are obtained from *Clostridium kluyveri*. Such genes have been located on a 7.5 kb DNA fragment (Söhling and Gottschalk, supra). In particular, this fragment contains the genes for a 4-hydroxybutyrate dehydrogenase (4hbD), a succinic semialdehyde dehydrogenase (sucD), and a acetyl-CoA:4-hydroxybutyrate CoA transferase (designated as orfZ in Söhling and Gottschalk, supra). The fragment also includes a membrane protein of unknown function (orfY) and a succinyl-CoA:CoA transferase, CAT1, that acts prior to the beginning of the succinyl-CoA metabolic pathway; CAT1 transfers CoA to succinate. Enzymes that act to produce succinyl-CoA, such as CAT1, can be found as a part of the citric acid cycle. Succinyl-CoA:CoA transferase can be encoded by a recombinant sequence, and included in the succinic semialdehyde metabolic pathway, in some embodiments of the present invention. Three of the proteins, 4HBD, SUCD, and ORFZ, were found to be expressed in *E. coli*.

In other preferred embodiments, the enzyme having 4-hydroxybutyrate dehydrogenase activity is obtained from *Ralstonia eutropha* (Valentin et al., *Eur. J. Biochem.* 227:43–60, 1995), the enzyme having acetyl-CoA:4-hydroxybutyrate CoA transferase activity is obtained from *Clostridium propionicum* (Schweiger and Buckel, *FEBS* 171:79–84, 1984), *Acidaminococcus fermentans* (Buckel et al., *Eur. J. Biochem.* 118:315–321, 1981), *Clostridium aminobutyricum* (Scherf and Buckel, *Appl. Environ. Microbiol* 57:2699–2702, 1991), or *Clostridium aminovalericum* (Eikmanns and Buckel, *Biol. Chem. Hoppe-Seyler* 371:1077–1082, 1990), and/or the enzyme having short chain fatty acid acyl-CoA synthetase activity is obtained from *Ralstonia eutropha* (Priefert and Steinbuchel, *J. Bact.* 174:6590–6599, 1992; Ohlrogge and Browse, *Plant Cell* 7:957–920, 1995).

As noted above, the present invention provides methods of producing PHAs comprising 4HB monomer units. In particular, the methods of the present invention include providing a host cell containing one or more recombinant sequences, which means introducing into a prokaryotic, plant or other host cell one or more vector constructs or other recombinant sequences as described herein, then culturing or growing the host cell under the host cell under suitable conditions to produce the PHA comprising 4HB monomer units. Suitable conditions will be readily identifiable by a person skilled in the art in light of the present specification, and include an appropriate medium that contains an appropriate carbon source, and growing the host cells for a time sufficient to obtain expression of the required sequences (i.e., production of gene product, typically enzymes) from the genes of the PHA biosynthetic pathway and succinic semialdehyde metabolic pathway, to produce the PHA comprising 4HB monomer units. The PHA can then be isolated from the host cell, which means separated from the host cell, for example where the PHA is not extruded or secreted by action of the host cell during or after its production within the host cell.

Preferably, the carbon source does not contain significant amounts of a structurally related precursor of 4-hydroxybutyrate, which means carbon sources that have the four carbon skeleton of 4-hydroxybutyrate and have a hydroxyl group on the fourth carbon. Examples of structurally related precursors of 4-hydroxybutyrate include 4-hydroxybutyrate, 1,4-butanediol or 4-butyrolactone.

Preferably, the carbon source is primarily comprised of a simple, inexpensive carbon source such as a sugar comprising a 5-carbon or 6-carbon ring. Preferred examples of such sugars include glucose, sucrose, fructose, lactose or cellulose. In an alternative embodiment, the carbon source consists essentially of such a simple, inexpensive carbon source, which means that no significant amounts of any structurally related precursors of 4-hydroxybutyrate are present in the carbon source.

The methods of the present invention are also useful because the composition of the PHA can be carefully controlled. For example, when using a *Nocardia corallina* PHA synthase, in a host cell also containing genes for 3-ketothiolase, acetoacetyl-CoA reductase and succinic semialdehyde metabolism, providing a carbon source comprising an even-numbered carbon chain (preferably an even-numbered fatty acid) will typically result in PHA that will comprise at least about 10% of the dry cell weight of the bacterial host cell and the PHA will largely comprise the terpolymer P(3HB-co-3HHx-co-4HB) and wherein the 3HHx comprises about 2–20 mol % of the polymer. Typically, the PHA will comprise at least about 15% of the dry cell weight, preferably at least about 20% of the dry cell weight, and further preferably at least about 24% of the dry cell weight. When the host cell is a plant cell, the PHA will generally comprise at least about 2% of the dry cell weight, typically at least about 3% of the dry cell weight, preferably at least about 4% of the dry cell weight, and further preferably at least about 5% of the dry cell weight. Also typically, the 3HHx comprises about 3–15 mol % of the terpolymer, preferably comprises about 5–10 mol % of the terpolymer, and further preferably comprises about 8 mol % of the terpolymer.

Alternatively, by providing a carbon source comprising an odd-numbered carbon chain (preferably an odd-numbered fatty acid) the resulting PHA will comprise at least about 10% of the dry cell weight of the bacterial host cell and the PHA will largely comprise the terpolymer P(3HV-co-3HHp-co-4HB) and wherein the 3HHp comprises about 2–20 mol % of the terpolymer. Typically, the PHA will comprise at least about 20% of the dry cell weight, preferably at least about 40% of the dry cell weight, and further preferably at least about 49% of the dry cell weight. When the host cell is a plant cell, the PHA will generally comprise at least about 2% of the dry cell weight, typically at least about 3% of the dry cell weight, preferably at least about 4% of the dry cell weight, and further preferably at least about 5% of the dry cell weight. Also typically, the 3HHp comprises about 3–15 mol % of the terpolymer, preferably comprises about 5–10 mol % of the terpolymer, and further preferably comprises about 8 mol % of the terpolymer.

In other embodiments, the methods can include providing a plurality of carbon sources in the feed during the culturing of the host cell, wherein the feed includes carbon sources having a selected ratio of a $C_4$ carbon source and a $C_6$ (or greater) even-numbered carbon source. In an alternative embodiment, a first carbon source comprises a $C_5$ carbon source and a second carbon source is a $C_7$ (or greater) odd-numbered carbon source. Varying the ratio of the amount of $C_4$ to $C_6$ carbon source (or greater) or the amount of $C_5$ to $C_7$ carbon source (or greater) in the feed permits control of the ratio of 3HB:3HHx:4HB in the P(3HB-co-3HHx-co4HB) terpolymer, or 3HB:3HHp:4HB in the P(3HV-co-3HHp-co-4HB) terpolymer (respectively), that is ultimately produced. For example, providing a feed having 10% $C_4$ carbon source and 90% $C_6$ carbon source (or greater) will result in a PHA having a high percentage of 3HHx, while providing a feed having 90% $C_4$ carbon source and 10% $C_6$ carbon source (or greater) will result in a PHA having a high percentage of 3HB. In another alternative embodiment, the feed can contain selected amounts of any combination of suitable carbon sources, regardless of even-number or odd-number of the carbon chain(s), to provide other desired polymers. Such feeds can contain more than two carbon sources, and the desired resulting polymers can contain more than two constituents. As one example, the feed can contain 35% $C_4$ carbon source, 35% $C_5$ carbon source and 30% $C_7$ carbon source, to provide a multipolymer comprising P(3HB-co-3HV-co-3HHp-co-4HB) having desired percentages of the 3HB, 3HV, and 3HHp. As another example, the feed can contain 35% $C_5$ carbon source, 35% $C_6$ carbon source and 30% $C_7$ carbon source, to provide a polymer comprising P(3HB-co-3HV-co-3HHx-co-3HHp) having desired percentages of the 3HB, 3HV, 3HHx and 3HHp. If desired, the 3HB component can be a relatively minor constituent if appropriate carbon sources are provided in the feed. Generally, the polymers can comprise components up to 3-hydroxyoctanoate (3HO), if at least $C_8$ carbon source is included in the feed source. However, even where carbon sources of $C_8$ carbon source or greater are used, the predominant species are typically primarily 3HB, 3HV, 3HHx and/or 3HHp, depending upon the carbon source. In some preferred embodiments, the carbon source is selected from $C_4$, $C_5$, $C_6$, $C_7$, $C_8$, $C_9$, $C_{10}$, $C_{12}$, $C_{14}$, $C_{16}$, and $C_{18}$ carbon sources.

In a preferred embodiment, the method, and the vectors used in the method, are selected such that culture medium does not include an antibiotic.

Once the host cell has been cultured or grown under conditions and for a time sufficient to generate PHA, the PHA is preferably isolated from the host cell. Isolation may be accomplished by a variety of methods. For example, the host cells may be lysed, and PHA agglomerated, essentially as described in U.S. Pat. No. 5,334,520. Alternatively, lysozyme plasmids may be introduced into the host cell, and thereby utilized to enhance isolation of PHA, essentially as described in PCT/US93/05187.

Within a preferred embodiment, typically with respect to prokaryotic host cells, after the host cells have reached the stationary phase of growth, they are washed once with water to remove debris. The cells are then heat sterilized, and while still hot, SDS (approximately 0.1%) and EDTA (approximately 2 mM) are added, and the mixture is stirred for about one hour at a temperature of 60° C. to 80° C. During this time, the cells will lyse, releasing the PHA granules. The granules are separated from cell debris by centrifugation, and then washed twice with water.

Through use of the above-described techniques, PHAs comprising 4HB monomer units may typically be isolated to greater than 70% purity, generally to greater than 80% purity, preferably to greater than 90% purity, and further preferably to approximately 98% or 99% purity, as determined by gas chromatography. Briefly, PHA purity may be calculated by determining the area under the PHA peak, and dividing it by the areas under all peaks in the chromatogram.

The PHA content in the experimental samples may be determined using methods known in the art, such as the following. Samples of host cells containing PHA are subjected to methanolysis by adding 1.7 ml of ACS grade methanol (mallinckrodt), 2 ml of ACS grade chloroform (mallinckrodt), 0.05 ml of benzoic acid (2 mg/ml) (Sigma), and then adding 0.3 ml of concentrated sulfuric acid (Fisher Scientific). Samples are capped tightly, placed in a heat-block adjusted to 100° C. and incubated for 140 minutes. Samples are then removed cooled to room temperature. 1 ml deionized water is then added to each tube, the tubes are vortexed for 30 seconds, and then centrifuged in a Varifuge RF centrifuge (Heraeus Instruments) for 10 minutes at 2500 rpm. The upper aqueous phase of each sample is removed by aspiration and the remaining organic phase is pipetted into vials and assayed for PHA production by gas chromatography, for example using a Shimadzu GC-14A, connected to a CR4A data processing unit, an AOC-14 autoinjector, and an AOC-1400 autosampler. The carrier gas is UPC grade helium and detection is through a flame ionization detector. The flow rate of the carrier is approximately 5 ml/min. The column used for detection is a Supelcowax 10 column (Supelco Separation Technologies). The column is a 15 meter column, 0.53 mm inner diameter, with a 1 $\mu$m thick coating. Samples (1 to 3 $\mu$l) are injected into the injection port (temperature 200° C.) and carried into the column. The samples are run under temperature profile of 55° C. for 5 minutes, followed by a temperature ramp of 5° C. per minutes until the column temperature reached 220° C. The temperature is held at 220° C. for 5 minutes, followed by a termination of the run and cool-down for the next run. Typically, the solvent peak eluted through the detector (240° C.) between 1 and 2 minutes, and the methyl esters of hydroxy-fatty acids derived from methanolysis of the PHA peak eluted between 3 and 25 minutes. Analyses are done using benzoic acid (100 $\mu$l of 2 mg/ml solution in methanolysis tubes) as an internal standard. Typically, benzoic acid eluted from the GC column approximately 5 minutes into the run.

PHA control samples are weighed out on Sartorius balance and subjected to methanolysis. The area under each curve (integration by Shimadzu data processor) is graphed against the known weights. The resulting line is used to generate an equation that can be used to calculate the PHA content in the experimental samples using the integration area under the PHA peak.

For dry weight determinations, 5.0 ml samples are removed from cultures and centrifuged for 10 minutes at 3000 rpm in a Varifuge RF centrifuge (Heraeus Instruments). The supernatant is removed by aspiration and the cell pellet is resuspended in 1.0 ml of 0.85% saline solution. This is added to a preweighed aluminum weigh boat and placed in a 80° C. drying oven for approximately 30 hours. The dry weight is calculated by subtracting the weight of the empty aluminum weigh boat and the weight of 1.0 ml of 0.85% saline from the total weight. This value is then divided by 5 to obtain the dry weight in mg/ml.

Within the context of the present invention, reference to the genes within the PHA biosynthetic pathway and the recombinant succinic semialdehyde metabolic pathway, and the other genes discussed herein such as the genes encoding succinic semialdehyde dehydrogenase, includes derivatives of the genes that are substantially similar to the genes (and, where appropriate, the proteins (including peptides and polypeptides) that are encoded by the genes and their derivatives). As used herein, a nucleotide sequence is deemed to be "substantially similar" if: (a) the nucleotide sequence is derived from the coding region of described genes; (b) the nucleotide sequence is capable of hybridization to nucleotide sequences of the present invention under high or very high stringency (see Sambrook et al., *Molecular Cloning: A Laboratory Manual,* 2nd ed., Cold Spring Harbor Laboratory Press, NY, 1989) or (c) the DNA sequences are degenerate as a result of the genetic code to the DNA sequences defined in (a) or (b). Further, the genes discussed herein include both complementary and non-complementary sequences, provided the sequences otherwise meet the criteria set forth herein. Within the context of the present invention, a nucleotide sequence is generally capable of hybridizing to the nucleotide sequence of (a) or (b) when hybridized at a temperature of 65° C. for sufficient time to permit hybridization, thereby providing a hybridization mixture, and then washed two times in 2XSSC, 0.1% SDS at room temperature and two times in 0.5X SSC, 0.1% SDS at 55° C. Typically, the nucleic acid molecule is capable of hybridizing when the hybridization mixture is washed at least one time in 0.1 XSSC at 65° C., preferably at 68° C., and further preferably at 71° C.

The genes discussed herein can be isolated from chromosomal DNA. Chromosomal DNA libraries constructed in vectors, such as bacteriophage vectors, such as λEMBL3, λgt10, cosmids or plasmids, are suitable for use. Such libraries can be constructed using methods and techniques known in the art (see Sambrook et al., *Molecular Cloning: A Laboratory Manual,* Cold Spring Harbor Press, 1989) or purchased from commercial sources (e.g., Clontech). One example of the construction of a library is set forth below in Example.

The genes discussed herein can also be isolated by PCR performed on chromosomal DNA or libraries, or by probe hybridization of genomic DNA libraries. Primers for PCR and probes for hybridization screening may be designed based on the DNA sequence of the desired gene. The primers preferably do not have self-complementary sequences nor do they have complementary sequences at their 3' end (to prevent primer-dimer formation). Preferably, the GC content of the primers is about 50% and the primers contain restriction sites. The primers are annealed to the DNA and sufficient cycles of PCR are performed to yield a product readily visualized by gel electrophoresis and staining. The primers are generally at least 16 nucleotides in length, typically at least 20 nucleotides in length, preferably at least 24 nucleotides in length, and further preferably at least 28 nucleotides in length. The primer is typically capable of specifically priming a desired gene, such the *Nocardia corallina pha* synthase gene, which means that, under appropriately amplification conditions, the probe primes only the *Nocardia corallina pha* synthase gene but does not prime the pha synthase genes of other organisms, such as the *Ralstonia eutropha, Pseudomonas putida* or *Rhodococcus ruber pha* synthase genes. The amplified fragment is purified and inserted into a vector, and propagated.

The gene products expressed from the genes discussed herein will typically be proteins. Such proteins may be in the form of an acidic or basic salt, or in neutral form. In addition, individual amino acid residues may be modified by oxidation or reduction. Furthermore, various substitutions, deletions, or additions may be made to the amino acid sequence, the net effect of which is to retain or further enhance or decrease the biological activity of the mutant or wild-type protein. Moreover, due to degeneracy in the genetic code, for example, there may be considerable variation in nucleotide sequences encoding the same amino acid sequence.

The structure of the proteins discussed herein can be predicted from the primary translation products using the hydrophobicity plot function of, for example, P/C Gene or Intelligenetics Suite (Intelligenetics, Mountain View, Calif.), or according to the methods described by Kyte and Doolittle (*J. Mol. Biol.* 157:105–132, 1982).

The genes and proteins discussed herein can be constructed using a wide variety of techniques known in the art. Further, mutations can be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion. Alternatively, oligonucleotide-directed site-specific (or segment specific) mutagenesis procedures may be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques,* January 1985, 12–19); Smith et al. (*Genetic Engineering: Principles and Methods,* Plenum Press, 1981); and Sambrook et al. (supra). Deletion or truncation derivatives can also be constructed by utilizing convenient restriction endonuclease sites adjacent to the desired deletion. Subsequent to restriction, overhangs may be filled in, and the DNA relegated. Exemplary methods of making the alterations set forth above are disclosed by Maniatis et al., *Molecular Cloning: A Laboratory Manual,* Cold Spring Harbor Laboratory, Cold Spring Harbor, N.Y., 1982, and Sambrook et al. (*Molecular Cloning: A Laboratory Manual,* 2d Ed., Cold Spring Harbor Laboratory Press, 1989). Other derivatives of the genes and proteins discussed herein include conjugates of the genes and proteins along with other genes, proteins or polypeptides, such as fusion peptides.

As noted above, in a further aspect the present invention provides vector constructs or expression vectors that express the PHA biosynthetic pathway, recombinant succinic semialdehyde metabolic pathway. As used herein, "vector construct" or "expression vector" refers to an assembly which is capable of directing the expression of the desired pathway, as well as any additional sequence(s) or gene(s) of interest. The vector includes transcriptional promoter elements that are operably linked to the genes of interest. The vector may be composed of either deoxyribonucleic acids ("DNA"), ribonucleic acids ("RNA"), or a combination of the two (e.g., a DNA-RNA chimeric). Optionally, the vector may include a polyadenylation sequence, one or more restriction sites, as well as one or more selectable markers. A variety of such markers are well known in the art. Additionally, depending on the host cell chosen and the vector employed, other genetic elements such as an origin of replication, additional nucleic acid restriction sites, enhancers, sequences conferring inducibility of transcription, and additional selectable markers, may also be incorporated into the vectors described herein. The constructs can be used such that all genes are present in a single construct, or the genes can be expressed from one or more additional constructs. Additionally, one of the pathways or other genes can be present within the chromosome of the host cell.

In a preferred embodiment, the vector construct comprises a strongly expressed and negatively regulated promoters operably linked to the desired gene. Such promoters can be controllably "turned on" and "turned off" by the introduction of an inducer or a derepressor into its host cell. When "turned on," such promoters permit substantially uninterrupted transcription of a gene (or operon) operably linked thereto (and such promoters are not repressed by substances found in the host cell). When "turned off," such promoters do not permit any substantial transcription of the gene. Methods for determining whether and when such promoters are "on" and "off." as well as the detection of gene products from the linked gene (such as mRNA, proteins or enzymes, or downstream products such as PHAs), are well known in the art, in light of the instant specification.

In one embodiment, the negatively regulated promoter preferably comprises the −35 region of the trp promoter operably linked to the −10 region of the lac promoter, and the operator region of the lac promoter (Russell and Bennett, *Gene* 20:231, 1982). The −35 region of a promoter typically comprises an approximately 6- to 12-base sequence centered around the −35 nucleotide (plus or minus two or three nucleotides, measured from the transcription initiation site). Further typically, the −35 region of the trp promoter includes the nucleotide sequence TTGACA (Darnell et al., *Mol. Cell Biol.*, 270–85, 1986). The −10 region, also known as a Pribnow box, typically comprises an about a 6-base sequence centered around the −10 nucleotide (plus or minus two or three nucleotides, also measured from the transcription initiation site). Further typically, the lac −10 region includes the nucleotide sequence TATAAT (Darnell, supra). In a preferred embodiment, the promoter is the tac promoter, although other promoters, such as the trc promoter (Borel et al., *FEBS* 324:162, 1993) that also comprise operable fusions of the −35 region of the trp promoter and the −10 region of the lac promoter, are also preferred embodiments. (See generally, Kidwell, J., Valentin, H. E., and Dennis, D., *Appl. Environ. Microbiol.* 61:1391–1398, 1995.)

Other negatively regulated promoters are also suitable for use within the vectors of the present invention, provided that such a promoter is repressed when present in lower numbers in a cell than the given promoter's repressor molecule, and that an increase in the copy number of operators (i.e., repressor binding sites) effectively titrates out the effects of the repressor molecules, thereby inducing transcription of the desired gene. One example of such a promoter is an unaltered trp promoter (Yansura and Henner, *Meth. Enz.* 185:54–61, 1990). Other promoters may also be utilized within the vector constructs, methods and other aspects of the invention. Whether a promoter is operable can be readily determined in light of the present specification, by screening for the presence or absence of PHA (for example, by examining cells under a light microscope for the presence of PHA), or for the presence or absence of mRNA produced from the desired gene (for example by hybridization assay).

In one example of a promoter useful in the present invention, initiation of transcription may be repressed by binding a repressor, such as the lacI gene product, to the operator, which is located between the promoter and the desired gene. In the presence of a chemical inducer, preferably isopropyl-β-D-thiogalactoside (IPTG), the repressor is converted to an inactive form, thereby permitting initiation of transcription from the promoter. Other suitable inducers will be apparent in light of the present specification. Such inducers may include glucose-β-galactoside (lactose), glucose-α-galactoside (melibiose), and other lactose analogues such as methyl-β-galactoside and methyl-β-thiogalactoside (Jacob and Monod, *J. Mol. Biol.* 3:318–356, 1961).

In a further aspect, the present invention provides the pathways and genes described herein incorporated into one or more runaway replicon vector constructs. A runaway replicon vector construct is a vector construct that can be controllably induced and that, upon induction, significantly increases its copy number in the cell. In one embodiment the copy number of the runaway replicon vector construct is controlled by temperature (Nordstrom and Uhlin, *Biotechnology* 10:661, 1992). In this preferred embodiment, the repA gene, which encodes a protein that is required for the initiation of plasmid replication, is under the control of the λ pR promoter. The λ cI857 gene encodes a heat-sensitive repressor that actively inhibits transcription from the λ pR promoter at low temperature, but that is inactive at high temperatures. Therefore, the incorporation of the λ cI857 gene in a host cell permits repression of the λ pR promoter at a low temperature. Thus, at low temperatures, such as 30° C., the vector construct copy number is low, while at high temperatures, such as 42° C., synthesis of repA mRNA increases, and the vector construct copy number is high.

In another embodiment, the runaway replicon vector construct further comprises a tac promoter operably linked to a *Ralstonia eutropha* (formerly *alcaligenes eutrophus*) PHA synthase gene, to provide a tac::pha fusion runaway replicon vector construct. The tac::pha fusion runaway replicon construct is a novel expression system in which the copy number and transcription of the *Ralstonia eutropha pha* synthase gene are both efficiently controlled by temperature, even when IPTG (or other derepressor or inducer) is not present. At low temperatures, the copy number of the vector construct is lower than the number of lacI repressor proteins present in the cell (such number is typically about 5–10 proteins per cell (Muller-Hill et al., *Proc. Natl. Acad. Sci.* 59:1259, 1968). Thus, the number of lacI repressor molecules is sufficient to substantially repress transcription of the *Ralstonia eutropha pha* synthase gene. At higher temperatures (which induce expression of the repA gene and therefore increase the copy number of the vector construct), the number of vector constructs surpasses the number of lacI repressor molecules. This rapidly results in non-repressed *Ralstonia eutropha pha* synthase genes, and provides the highly advantageous, and unexpected result, that the *Ralstonia eutropha pha* synthase genes are then expressed without the addition of an inducer such as IPTG. This system also provides the highly advantageous, and unexpected, result that the system is stable without the selective pressure of antibiotics to retain the vector construct (although the system preferably includes a stabilization locus, discussed further below, this advantageous and unexpected result may also be found in systems without a stabilization locus).

In another aspect, the present invention provides vector constructs in which the native Shine-Dalgarno sequence for the desired gene is supplemented by or replaced with a consensus Shine-Dalgarno sequence, preferably the lac Shine-Dalgarno sequence. A Shine-Dalgarno sequence is a sequence located about 5 to 10 bases to the 5' side of the start codon (typically AUG) of an mRNA sequence (Zubay, *Biochemistry*, 944–45, 1983). In a preferred embodiment, the consensus Shine-Dalgarno sequence comprises AGGA, although other suitable Shine-Dalgarno sequences could be easily utilized by a person having ordinary skill in the art in light of the present specification. Determination of the effectiveness of a Shine-Dalgarno sequence is also well within the skill of the art in light of the present specification, for example by screening for mRNA copy number (see PCT/US95/01433; PCT/US95/01471).

In yet another embodiment, the present invention provides vector constructs, such as those described above, further comprising a stabilization locus. Suitable stabilization loci include parB (Gerdes, K., Bio/Technology 6:1402–1405, 1988), ccd, which appears to operate by a mechanism that involves post-segregational mortality of cells that lose a plasmid carrying the ccd locus (Gerdes, supra), the pemK/pemI system (Tsuchimoto, S. et al., J. Bact. 170:1461–1466, 1988), which also appears to involve mortality of plasmid-free segregants, and the plasmid maintenance system found in the F factor and encoded by the sopA, sopB, and sopC genes (Ogura and Hiraga, Cell 32:351–360, 1983). The provision of such a stabilization locus promotes stability of a desired plasmid in a cell. Determination of other suitable stabilization loci, in light of the present specification, that would be suitable for use with the vector constructs, methods and other aspects of the present invention is within the skill of the art. See U.S. Pat. No. 5,512,456.

The present invention also provides host cells containing one or more recombinant nucleic acid sequences encoding one or more genes from the PHA biosynthetic pathway and the succinic semialdehyde metabolic pathway. The present invention further provides for the manipulation and expression of one or more desired genes within such host cells by cultivating host cells, which includes culturing and/or growing the host cells, containing a construct capable of expressing the desired gene, including substantially similar derivatives thereof. Methods for producing recombinant protein, which leads to the production of PHA, in a variety of prokaryotic and eukaryotic host cells are generally known in the art (see, Methods in Enzymology, Vol. 185, Goeddel (ed.), Academic Press, San Diego, Calif., 1990; see also, Methods in Enzymology, Guthrie and Fink (eds.), Academic Press, San Diego, Calif., 1991).

With respect to prokaryotic host cells, such cells are transformed by vector constructs such as those described above. Various prokaryotic host cells can be utilized within the context of the present invention. Generally, preferred prokaryotic host cells should have a well-characterized genetic system, including known cloning vectors and methods of genetic manipulation. They should also preferably grow well in minimal medium, ideally to a high cell density, without any special requirements (physical or physiological). Representative examples of such host cells include members of the Bacillaceae, Nocardiaceae, Streptomycetaceae, Pseudomonadaceae, Corynebacteria, Enterobacteriaceae, Agrobactericeae, Rhodococcus and Rhizobia. In a preferred embodiment, the host cell is able to metabolize sucrose. Preferred host cells in the Family Enterobacteriaceae include Escherichia, Citrobacter, Klebsiella, Enterobacrer, and Serratia, as well as Zymomonas and Flavobacterium, which are within the Enterobacteriaceae but of uncertain affiliation. Other preferred host cells include Ralstonia eutropha. Particularly preferred host cells include E. coli, Klebsiella oxytoca, and Klebsiella aerogenes. Preferred host cells in the Family Pseudomonaceae include P. aeruginosa and P. putida. Other preferred host cells include Rhodococcus ruber and Bacillus megaterium.

Such prokaryotes may be readily obtained from a variety of commercial sources including, for example, the American Type Culture Collection (ATCC) (Rockville, Md.). Alternatively, many of the above-described bacteria may be isolated from sources that are known by those of skill in the art to contain such prokaryotes, based upon techniques that are known in the art. (See Bergy's Shorter Manual of Determinative Bacteriology, Williams & Wilkins (pub.), John G. Holt (ed.), 8th edition, 1977.)

Numerous plant host cells and vectors known in the art can also be useful within the present invention, in light of the subject specification. For example, the use of Agrobacterium rhizogenes as vectors for expressing genes in plant cells has been reviewed by Sinkar et al., (J. Biosci. (Bangalore) 11:47–58, 1987). Plants containing one or more recombinant sequences encoding the PHA biosynthetic pathway and/or the succinic semialdehyde metabolic pathway are known as transgenic plants. Preferably, such plants include the recombinant sequences in their germ cells, which are the cells of sexual reproduction.

An example of a plant suitable for use within the present invention is Arabidopsis thaliana. (Nawrath, C., Proc. Natl. Acad. Sci. 91:12960–64, 1994; Poirier, Y., et al., Science 256:520–523, 1992). The use of plant cells can be particularly advantageous because the PHA biosynthetic pathway can utilize the fatty acid degradation or fatty acid biosynthesis pathways in plants, which in some plants results in the accumulation of fatty acids in the form of oils to levels as high as 30 to 40% of their weight (Ohlrogge, J. B., Jaworski, J. G. and Post-Beittenmiller, Lipid Metabolism In Plants, 1:3–33 (CRC Press, Moore, T. S., ed., 1993). (See also Eschenlauer, A. C. et al., Abstr. Annu. Meet. International Symposium on Bacterial Polyhydroxyalkanoates, Montreal, Canada, 85:66, 1994; Hahn, J. J., Abstr. Annu. Meet. International Symposium on Bacterial Polyhydroxyalkanoates, Montreal, Canada, 82:65; Landschulze, V. et al., Abstr. Annu. Meet. International Symposium on Bacterial PHA, Montreal, Canada, 86:66; Nawrath, C. et al., Abstr. Annu. Meet. International Symposium on Bacterial Polyhydroxyalkanoates, Montreal, Canada, 83, 1994; Poirier, Y., Adv. Mater. 5:30–36, 1993; Pool, R., Science 245:1187–1189, 1989; Poirier, Y., Sci. 256:520–523, 1992; Nawrath, C., Proc. Natl. Acad. Sci. 91:12760–64, 1994).

The construction of transformation vectors capable of introducing, and expressing (if desired) the genes discussed herein related to PHA biosynthesis in plants can be performed as follows. Generally, such vectors comprise a selectable marker and one or more coding sequences of interest under the transcriptional control of 5' and 3' regulatory sequences. Such regulatory sequences can include a promoter, a transcription initiation start site, an RNA processing signal, a transcription termination site, and/or a polyadenylation signal. A Plant promoter can be inducible or constitutive, environmentally- or developmentally-regulated, or cell- or tissue-specific. Often-used promoters include the CaMV 35S promoter (Odell et al., Nature 313:810, 1985), the enhanced CaMV 35S promoter, the Figwort Mosaic Virus (FMV) promoter (Richins et al., NAR 20:8451, 1987), the mannopine synthase (mas) promoter, the nopaline synthase (nos) promoter, and the octopine synthase (ocs) promoter. Useful inducible promoters include heat-shock promoters (Ou-Lee et al., Proc. Natl. Acad. Sci. USA 83:6815, 1986; Ainley et al., 1990), a nitrate-inducible promoter derived from the spinach nitrite acetoacetyl-CoA reductase gene (Back et al., Plant Mol Biol 17:9, 1991) hormone-inducible promoters (Yamaguchi-Shinozaki et al., Plant Mol Biol 15:905, 1990; Kares et al., Plant Mol Biol 15:905, 1990), and light-inducible promoters associated with the small subunit of RuBP carboxylase and LHCP gene families (Kuhlemeier et al., Plant Cell 1:471, 1989; Feinbaum et al., Mol. Gen. Genet. 276:449, 1991; Weisshaar et al., EMBO J. 10:1777, 1991; Lam and Chua, Science 248:471, 1990; Castresana et al., EMBO J. 7:1929, 1988; Schulze-Lefert et al., EMBO J. 8:651, 1989). Examples of useful tissue-specific, developmentally-regulated promoters include the β-conglycinin 7S promoter (Doyle et al., J. Biol.

Chem. 261:9228, 1986; Slighton and Beachy, *Planta* 172:356, 1987), and seed-specific promoters (Knutzon et al., *Proc. Natl. Acad. Sci. USA* 89:2624, 1992; Bustos et al., *EMBO J.* 10:1469, 1991; Lam and Chua, *Science* 248:471, 1991; Stayton et al., *Aust. J. Plant. Physiol.* 18:507, 1991). Plant functional promoters useful for preferential expression in seed plastids include those from plant storage protein genes and from genes involved in fatty acid biosynthesis in oilseeds. Examples of such promoters include the 5' regulatory regions from such genes as napin (Kridl et al., *Seed Sci Res.* 1:209, 1991), phaseolin, zein, soybean trypsin inhibitor, ACP, stearoyl-ACP desaturase, and oleosin. Seed-specific gene regulation is discussed in EP 0 255 378. Promoter hybrids can also be constructed to enhance transcriptional activity (Hoffman, U.S. Pat. No. 5,106,739), or to combine desired transcriptional activity and tissue specificity. Representative vectors typically comprise, operatively linked in the 5' to 3' direction, a promoter sequence that directs the transcription of a downstream heterologous structural nucleic acid molecule (typically DNA) in a plant. Optionally, a non-translated leader sequence; a nucleotide sequence that encodes a protein of interest; and a 3' non-translated region that encodes a polyadenylation signal that functions in plant cells to cause the termination of transcription and the addition of polyadenylate nucleotides to the 3' end of the mRNA encoding said protein.

The vector can also be constructed to take advantage of desired timing and intracellular localization of expression from the genes (and the expression of other enzymes useful for the biosynthesis of PHA). For example, if fatty acid biosynthetic pathways are utilized in oilseed plants such as canola, then expression from the genes of the PHA biosynthetic pathway should be concurrent with fatty acid biosynthesis and targeted to the seed leucoplast or leaf chloroplast.

A variety of different methods can be employed to introduce desired vectors into preferred sites within the plant to generate transgenic plants. Preferred sites within the plant include plant protoplasts, cells, callus tissue, leaf discs, and meristems. Methods of introducing the desired vector include Agrobacterium-mediated transformation, particle gun delivery, microinjection, electroporation, polyethylene glycol-mediated protoplast transformation, and liposome-mediated transformation. A general review of such methods is found in Potrykus, *Annu. Rev. Plant Physiol. Plant Mol. Biol.* 42:205–225, 1991.

Transgenic plants comprising cells containing the genes discussed herein, can be produced, for example, by transforming plant cells with a vector construct as described above, selecting plant cells that have been transformed on a selective medium, regenerating plant cells that have been transformed to produce differentiated plants, and selecting a transformed plant that expresses the genes by detecting appropriate signals, such as PHA synthesis or antibody binding of the proteins of the PHA biosynthetic pathway and/or the succinic semialdehyde metaboic pathway.

PHAs can be produced in plants by expression of the appropriate enzymes in the cytoplasm (Poirier et al., *Science* 256:520, 1992). Preferably, such production is targeted to the plastids, where higher levels of PHA production may typically be achieved: Targeting of 3-ketothiolase, acetoacetyl-CoA reductase, and PHA synthase to plastids of *Arabidopsis thaliana* has resulted in the accumulation of high levels of P(3HB) in the plastids without any readily apparent deleterious effects on plant growth and seed production. (Nawrath et al., *Proc. Natl. Acad. Sci. USA* 91:12760–12764, 1994). There is a high carbon flux through acetyl-CoA in plastids, especially in seeds of oil-accumulating plants such as oilseed rape (*Brassica napus*), canola (*Brassica rapa, Brassica campestris, Brassica carinata*, and *Brassica juncea*), soybean (*Glycine max*), flax (*Linum usitatissimum*), and sunflower (*Helianthus annuus*), for example, so targeting of the gene products for PHA-production to leucoplasts of seeds, or transformation of seed leucoplasts and expression therein of nucleic acid molecules encoding such gene products, are preferred strategies for achieving high levels of PHA biosynthesis in plants.

The gene products discussed herein for PHA production can be modified for plastid targeting by employing plant cell nuclear transformation constructs wherein nucleic acid sequences of interest are fused to any of the available transit peptide sequences capable of facilitating transport of the encoded enzymes into plant plastids (von Heijne et al., *Plant Mol. Biol. Rep.* 9:104, 1991), and driving expression by employing an appropriate promoter. Nucleic acid sequences that encode a transit peptide region can be obtained, for example, from plant nuclear-encoded plastid proteins, such as the small subunit (SSU) of ribulose bisphosphate carboxylase, plant fatty acid biosynthesis related genes including acyl carrier protein (ACP), stearoyl-ACP desaturase, β-ketoacyl-ACP synthase and acyl-ACP thioesterase, or LHCPII genes. The encoding sequence for a transit peptide effective in transport to plastids can include all or a portion of the encoding sequence for a particular transit peptide, and may also contain portions of the mature protein encoding sequence associated with a particular transit peptide. Numerous examples of transit peptides that can be used to deliver target proteins into plastids exist, and the particular transit peptide encoding sequences useful in the present invention are not critical as long as delivery into a plastid is obtained. Proteolytic processing within the plastid then produces the mature enzyme. (Nawrath et al., *Proc. Natl. Acad. Sci. USA* 91:12760–64, 1994.)

Preferably, the transit peptide sequences are derived from enzymes that are imported into the leucoplasts or chloroplasts of seeds or leaves. Examples of such enzymes include those related to lipid biosynthesis (e.g., subunits of the plastid-targeted dicot acetyl-CoA carboxylase, biotin carboxylase, biotin carboxyl carrier protein, a-carboxytransferase, plastid-targeted monocot multifunctional acetyl-CoA carboxylase (Mr, 220,000), plastidic subunits of the fatty acid synthase complex (e.g., acyl carrier protein (ACP), malonyl-ACP synthase, KASI, KASII, KASIII, etc.), steroyl-ACP desaturase, thioesterases (specific for short, medium, and long chain acyl ACP), plastid-targeted acyl transferases (e.g., glycerol-3-phosphate: acyl transferase), enzymes involved in the biosynthesis of aspartate family amino acids, phytoene synthase, gibberellic acid biosynthesis (e.g., ent-kaurene synthases 1 and 2), sterol biosynthesis (e.g., hydroxy methyl glutaryl-coA acetoacetyl-CoA reductase), and carotenoid biosynthesis (e.g., lycopene synthase).

Exact translational fusions to the transit peptide of interest may not be preferred for protein import into the plastid. However, creating translational fusions of the gene products discussed herein) to the precursor form of a naturally imported protein or C-terminal deletion thereof may aid in the uptake of the engineered precursor protein into the plastid. For example, Nawrath et al., *Proc. Natl. Acad. Sci. USA* 91:12760, 1994, used a similar approach to create the vectors employed to introduce the PHA biosynthesis genes of *A. eutrophus* into Arabidopsis.

Thus, in one preferred embodiment, the genes and gene products discussed herein are targeted to leaf chloroplasts or seed plastids such as leucoplasts by fusing the given gene to transit peptide gene sequences, in order to further enhance in vivo conditions for the biosynthesis of PHAs in plants.

In an alternative preferred embodiment, the genes can be expressed in situ in plastids by direct transformation of plastids with appropriate recombinant expression constructs. Vector constructs and methods for stably transforming plastids of higher plants are well known in the art (Svab et al., *Proc. Natl. Acad. Sci. USA* 87:8526, 1990; Svab and Maliga., *Proc. Natl. Acad. Sci. USA* 90:913, 1993; Staub and Maliga., *EMBO J.* 12:601, 1993; PCT International Publication WO 95/16783). These methods generally rely on particle gun delivery of the vector construct (which preferably contains a selectable marker in addition to the genes, and targeting of the DNA to the plastid genome through homologous recombination. A wide variety of different monocots and dicots can be transformed by particle gun bombardment (Hinchee et al., in: *Plant Cell and Tissue Culture*, I. Vasil and T. Thorpe (Eds), Kluwer Academic Publishers, Netherlands, p. 231, 1994).

Vector constructs for plastid transformation generally comprise a targeting segment comprising flanking nucleic acid sequences substantially homologous to a predetermined sequence of a plastid genome, which targeting segment enhances insertion of the vector sequences of interest into the plastid genome by homologous recombination with the genomic sequence; a selectable marker sequence disposed within said targeting segment, such as a sequence encoding a form of plastid 16S ribosomal RNA that is resistant to spectinomycin or streptomycin, or that encodes a protein which inactivates spectinomycin or streptomycin (such as the aadA gene), wherein the selectable marker sequence confers a selectable phenotype upon plant cells because substantially all the plastids of the cells will have been transformed with the vector construct; and, one or more nucleic acid coding sequences of interest disposed within the targeting segment relative to the selectable marker sequence so as not to interfere with conferring of the selectable phenotype. In addition, plastid expression vector constructs also generally include a plastid promoter region and a transcription termination region capable of terminating transcription in the plastid, wherein the regions are operatively linked to the nucleic acid coding sequences of interest.

A further refinement in chloroplast transformation/expression technology that facilitates control over the timing and tissue pattern of expression of introduced DNA coding sequences in plant plastid genomes has been described in PCT International Publication WO 95/16783. This method involves the introduction into plant cells of constructs for nuclear transformation that provide for the expression of a viral single subunit RNA polymerase and targeting of this polymerase into the plastids via fusion to a plastid transit peptide. Transformation of plastids with DNA constructs comprising a viral single subunit RNA polymerase-specific promoter specific to the RNA polymerase expressed from the nuclear expression constructs operably linked to DNA coding sequences of interest permits control of the plastid expression constructs in a tissue and/or developmental specific manner in plants comprising both the nuclear polymerase construct and the plastid expression constructs. Expression of the nuclear RNA polymerase coding sequence can be placed under the control of either a constitutive promoter, or a tissue- or developmental stage-specific promoter, thereby extending this control to the plastid expression construct responsive to the plastid-targeted, nuclear-encoded viral RNA polymerase. The introduced DNA coding sequence can be a single encoding region, or may contain a number of consecutive encoding sequences to be expressed as an engineered or synthetic operon. The latter is especially attractive where, as in the present invention, it is desired to introduce multigene biochemical pathways into plastids. This approach is not practical using standard nuclear transformation techniques since each gene introduced therein must be engineered as a monocistron, including an encoded transit peptide and appropriate promoter and terminator signals. Individual gene expression levels may vary widely among different cistrons, thereby possibly adversely affecting the overall biosynthetic process. This can be avoided by the chloroplast transformation approach.

The plant vector constructs discussed above can be utilized within plants according to a variety of strategies in order to produce transgenic plants capable of biosynthesizing high levels of PHAs. Such strategies can include the following:

(1) Transform individual plants with different desired vector constructs (for example, one vector construct may encode the PHA biosynthetic pathway, while a second may encode the succinic semialdehyde metabolic pathway). Two or more transgenic plants, each containing one of these vector constructs, are then grown and cross-pollinated so as to produce hybrid plants containing the two vector constructs. If necessary, the hybrid can then be crossed with the other transgenic plants in order to obtain a hybrid plant containing all nucleic acid molecules of interest within its genome.

(2) A single plant can be sequentially transformed with multiple vector constructs each containing one of the encoding nucleic acid molecules of interest.

(3) A single plant can be simultaneously cotransformed with multiple vector constructs each containing one of the encoding nucleic acid molecules of interest.

(4) A single plant can be transformed with a single vector construct containing all of the nucleic acid molecules of interest.

(5) Plants can also be transformed by a combination of any of the foregoing techniques in order to obtain a plant that expresses a desired combination of encoding nucleic acid molecules of interest.

As indicated in method 1 above, traditional breeding of transformed plants produced according to any one of the foregoing methods by successive rounds of crossing can incorporate all desired encoding nucleic acid molecules of interest in a single homozygous plant line (Nawrath et al., *Proc. Natl. Acad. Sci. USA* 91:12760, 1994; PCT International Publication WO 93/02187). Similar strategies can be employed to produce bacterial host cells engineered for optimal PHA production.

Particularly where different vector constructs are used to convey different desired nucleic acid molecules of interest, it is preferred to use different selectable marker genes in each of the vector constructs to facilitate selection of plants containing two or more different vector constructs. Examples of useful selectable marker genes include those conferring resistance to kanamycin, hygromycin, sulphonamides, glyphosate, bialaphos, and phosphinothricin.

In still another aspect, the present invention provides PHA produced in accordance with the above discussion using the PHA biosynthetic pathway and the succinic semialdehyde metabolic pathway. For example, such PHA has a particularly high molecular weight combined at a low polydispersity. Generally, the molecular weight is greater than about 600,000 daltons, typically greater than about 800,000 daltons, preferably greater than about 1,000,000 daltons and further preferably greater than about 1.2, 1.5 or 2.0 million daltons. Generally, the polydispersity is less than about 2, typically less than about 1.6, preferably less than about 1.5, and further preferably less than about 1.4 or 1.3.

The following Examples are offered by way of illustration, and not by way of limitation.

EXAMPLES

Example 1

Construction of Plasmids Suitable for the Production of P(3HB-co-4HB)

The plasmid pJM9238 is a runaway replication vector containing the genes for the PHA biosynthetic pathway from *Ralstonia eutropha* and has been previously described (Kidwell et al., *Appl. Env. Microbiol.* 61:1391–1398, 1995).

The plasmid pCKS carries the genes for the succinate metabolic pathway (which includes the succinic semialdehyde metabolic pathway) from *Clostridium kluyveri* and is a derivative of pck3psk which has previously been described (Söhling and Gottschalk, *J. Bact.* 178:871–880, 1996). To make pCKS, the plasmid pck3psk was subjected to partial EcoRI digestion and a 9.4 kb fragment was excised from a gel and ligated. This plasmid, pck3pskΔ, contained the genes for the succinate metabolic pathway minus an approximately 1.1 kb EcoRI fragment which encodes a putative membrane spanning protein of unknown function and the amino terminal region of cat1 (succinyl-CoA:CoA transferase). The insert that remained was removed by digesting with ApaI and SacI and was cloned back into pBluescript II-SK (Stratagene, La Jolla, Calif.) such that lacZ promoter promoted transcription in the same direction as the 3 intact genes on the insets (4hbD, sucD, orfZ).

Example 2

Growth of Cells for the Production of P(3HB-co-4HB) and P(4HB)

*E. coli* DH5α F-φ80dlacZΔM15 Δ(lacZYA-argF)U169 deoR recA1 endA1 phoA hsdR17($r_K^-$, $m_K^+$) supE44λ-thi-1 gyrA96 relA1 was used as a host cell (GibcoBRL, Bethesda, Md.). The cells used in these experiments were cultured overnight in 16×100 mm sterile tubes containing 3 ml of LB and the appropriate antibiotics (chloramphenicol at 25 μg/ml for pJM9238, ampicillin at 100 μg/ml for pCKS). In the morning, 1 ml of the overnight culture was used to inoculate 50 ml of the same media and 1% w/v) glucose in 300 ml baffled shake flasks. The cultures were grown at 30° C. until they reached an optical density of 0.7 (600 nm), at which time the cultures were shifted to an orbital incubator that was at 37° C. to induce pJM9238 into runaway replication. Cells were harvested after approximately 48 h of incubation at 37° C.

Example 3

Gas Chromatographic Analysis of PHA Produced in *E. coli* (pJM9238, pCKS)

*Escherichia coli* (pJM9238) and *Escherichia coli* (pJM9238, pCKS) were cultured in LB containing glucose to promote PHA synthesis and provide substrates for glycolysis and the TCA cycle. The cells were collected 48 h after induction of PHA accumulation, then harvested by centrifugation at 3,500 rpm (Heraeus Varafuge F) followed by suspension of the pellet in 0.9% (w/v) saline and recentrifugation to obtain a washed pellet. The washed pellet was frozen and dried by lyophilization. Intracellular PHA was characterized using a previously described modification (Slater et al., *Appl. Env. Microbiol.* 58:1098–1094, 1992) of the gas chromatographic method developed by Braunegg et al., *Eur. J. Microbiol. Biotechnol.* 6:29–37, 1978. P(3HB) (Sigma Chemicals) and γ-butyrolactone were used as standards. The results of this analysis are set forth in Table 1:

TABLE 1

P(3HB-co-4HB) accumulation in recombinant *E. coli*

| Plasmids | IPTG | mg cells | mol % 3HB | mol % 4HB | % PHA |
| --- | --- | --- | --- | --- | --- |
| pJM9238 | 0 | 84 | 100.0 | 0.0 | 52 |
| pJM9238, pCKS | 0 | 26 | 98.5 | 1.5 | 46 |
| pJM9238, PCKS[a] | 5 mM | 20 | 98.7 | 1.3 | 45 |

[a]Culture contained 2% (w/v) glucose rather than 1% (w/v) as in other cultures.

An extremely large amount of dried cell pellet from the (pJM9238) cultures was analyzed (84 mg), but no 4HB monomers could be detected in the polymer (P(3HB)) produced by such cultures. The overall level of P(3HB) (52% of cell dry weight) was consistent with previous experiments using this vector and host (Kidwell, J., Valentin, H. E., and Dennis, D., *Appl. Environ. Microbiol.* 61:1391–1398, 1995). When *E. coli* (pJM9238, pCKS) was analyzed (carrying the PHA biosynthetic pathway and the succinate metabolic pathway), very small peaks were observed on the chromatogram that corresponded exactly to the retention times of the 4HB standard, indicating the presence of 4HB in a P(3HB-co-4HB) polymer. The final level of 4HB in the P(3HB-co4HB) polymer was 1.5 mol %.

To determine if the succinate metabolic genetic pathway on pCKS was under the control of the lac promoter upstream of the genes, the experiment was also done in the presence of IPTG (added at the time of temperature upshift) to induce the lac promoter. The level of 4HB in the polyester was virtually unchanged (1.3 mol %), indicating that the lac promoter probably did not play a role in the expression of the succinate metabolic genes. When the original plasmid, pCK3pSK (which contains the succinate metabolic pathway of *C. kluyveri* in the opposite orientation from the lac promoter) was used in a similar experiment, only 0.2 mol % 4HB was found in the P(3HB-co-4HB) polymer.

Example 4

Isolation of the PHA from the Host Cells

The polymer was extracted from the host cells by shaking the dried bacterial cell pellet overnight at 37° C. in chloroform, removing the bacterial debris by filtration of the chloroform/bacterial suspension through Whatman paper, and precipitating the polyester from the filtered solution by the addition of 10 volumes of ethanol. The precipitated polymer was redissolved in chloroform, reprecipitated with 10 volumes of methanol, collected by centrifugation, placed onto a Whatman paper filter, and allowed to dry. The polymer was redissolved in deuterochloroform or chloroform and used for nuclear magnetic resonance and gel permeation chromatography analysis, respectively.

Example 5

$^1$H- and $^{13}$C{$^1$H}-NMR Analyses of the Isolated PHA

Because the level of 4HB in the polymer was quite low, confirmation of its presence was sought by nuclear magnetic resonance spectrometry of the purified polymer. For NMR analysis a larger culture (500 ml) of *E. coli* (pJM9238, pCKS) was grown under conditions described in the materials and methods except that the culture contained 2% glucose. The culture yielded 439 mg of cell dry mass from which 115 mg of PHA was extracted.

Nuclear magnetic resonance studies were done using a Bruker AC/200 spectrometer. The $^1$H spectrum (200 MHz) was obtained at 22° C. on a solution of polymer that was dissolved at a concentration of approximately 20 mg/ml in deuterochloroform. Pulses were taken using a 45° pulse width, 2.46 s acquisition time, 3333 Hz spectral width, 16K data points and 64 accumulations. Chemical shifts were measured relative to CHCl$_3$ (Δ=7.24 ppm). The $^{13}$C{$^1$H} spectra (50 MHz) were taken at 22° C. (on a polymer solution dissolved in deuterochloroform at approximately 50 mg/ml). The spectra were obtained using Waltz-decoupling, 30° pulses, 1 s relaxation delay, 12 kHz spectral width, 32k data points and 93,000 accumulations. Chemical shifts were measured relative to CDCl$_3$ (Δ=77.0 ppm).

Figure 2A:
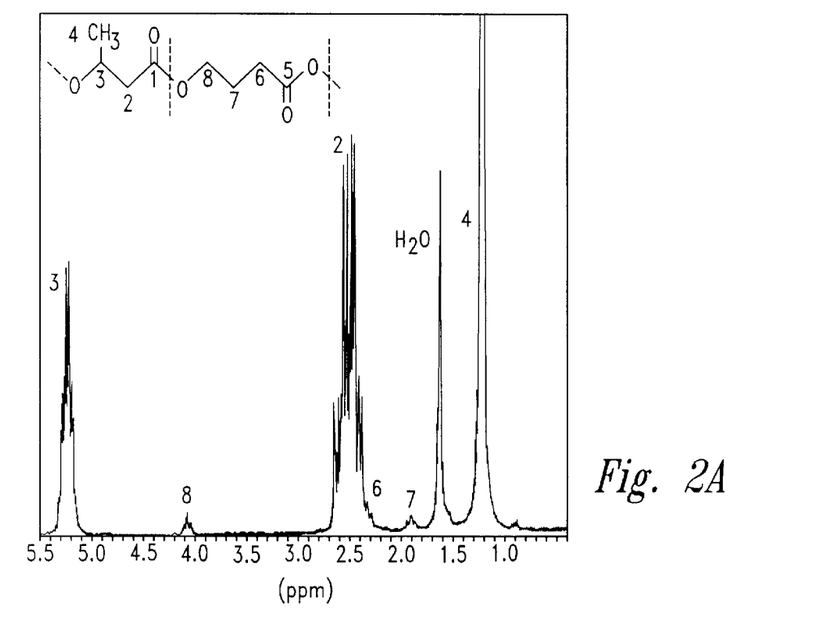
FIGS. 2A and 2B depict $^1$H-NMR (A) and $^{13}$C$\{^1$H$\}$-NMR (B) gas chromatography of purified P(3HB-co-4HB) polymer.
Figure 2B:
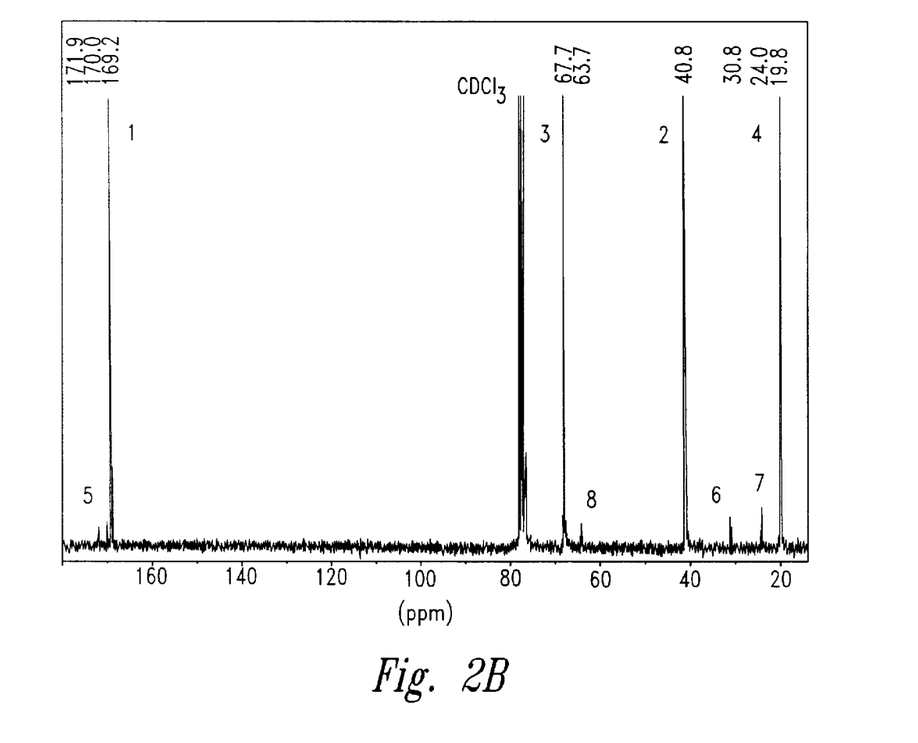

The results of the analyses are set forth in the spectrographs in FIGS. 2A and 2B. Both spectrographs displayed a pattern of signals virtually identical to spectra of P(3HB-co-4HB) that have been previously published (Doi et al., *Macromolecules* 21:2722–2727, 1988; Steinbüchel et al., *J. Env. Pol. Deg.* 2:67–74, 1994). Signals 6, 7, and 8 represent the $^1$H resonances of the corresponding 4HB-methylene groups (FIG. 2A). The $^{13}$C-{$^1$H}-NMR signals of the 4HB carbonyl carbon (signal 5) and the methylene carbons (signals 6, 7, and 8) can be seen in FIG. 2B at 171.9, 30.8, 24.0, and 63.7 ppm, respectively. Using the integration data from the $^1$H-NMR, the composition of the polymer was found to be 97.2 mol % 3HB and 2.8 mol % 4HB. As in the gas chromatographic analysis, no other signals were seen that could be interpreted to be additional polyhydroxyalkanoates resident in the polymer. The 4HB was produced despite the deletion of the succinyl-CoA:CoA transferase gene which is necessary for succinate degradation in *Clostridium kluyveri*. This is apparently due to the high flux of intracellular succinyl-CoA, and its availability, through the TCA cycle.

Example 6

Gel Permeation Chromatography of the Isolated PHA to Determine the Molecular Weight of P (3HB-co-4HB) from *E. coli* (pJM9238, pCKS)

To determine the molecular weight of the P(3HB-co-4HB) polymer, a portion of the extracted polymer isolated for the NMR experiment was subjected to gel permeation chromatography in accordance with the methods set forth in Koizumi et al., *J.M.S. Pure Appl. Chem.* A32:759–774, 1995. The estimated molecular weight of the polymer was $1.8 \times 10^6$ daltons. Previous analyses of poly-3-hydroxybutyrate extracted from recombinant *E. coli* (pJM9238) had shown that the molecular weight of the polymer usually was in the range of 1.0 to $3.0 \times 10^6$ (Kidwell et al., *Appl. Environ. Microbiol.* 61:1391–1398, 1995). Thus, it appears that it is possible to produce a high molecular weight polymer of P(3HB-co-4HB) in recombinant systems.

Example 7

Production of P(3HB-co-4HB) in CoA-Independent NAD- and CoA-Independent Dehydrogenase-Deficient Strains pJM9238 and pCKS were transformed into *E. coli* CT101 (Cooper, R. A. and Skinner, M. A., *J. Bact.* 43:302–306, 1980, Skinney, A. S. and Cooper, R. A., *Arch. Microbiol.* 132:270–275, 1982), a strain that is unable to express its own genomic CoA-independent NAD-dependent succinate semialdehyde dehydrogenase under conditions essentially as set forth in the Examples above. Gas chromatography showed the production of P(3HB-co-4HB) having 5 mol % 4HB which had been isolated from the cells.

Next, a second *E. coli* strain having a down-regulating mutation in its own CoA-independent NADP-dependent succinic semialdehyde dehydrogenase is transformed into the first strain. This results in an *E. coli* that has no functional, native CoA-independent NAD- or NADP-dependent succinic semialdehyde dehydrogenase. Suitable strains are available at the *E. Coli* Genetic Stock Center, New Haven, Conn. The P(3HB-co-4HB), and/or other PHAs, are obtained from the cells as above.

The present embodiments of the present invention are to be considered in all respects as illustrative and not restrictive, the scope of the invention being indicated by the appended claims rather than by the foregoing description, and all changes that come within the range and equivalency of the claims are therefore intended to be embraced therein.

What is claimed is:

1. A process for producing a polyhydroxyalkanoate comprising 4-hydroxybutyrate monomer units, the method comprising:

providing a host cell containing at least one recombinant nucleotide sequence that encodes a polyhydroxyalkanoate biosynthetic pathway, and at least one recombinant nucleotide sequence that encodes a succinic semialdehyde metabolic pathway that metabolizes succinic semialdehyde via a 4-hydroxybutyryl-CoA intermediate; and, cultivating the host cell under suitable conditions to obtain expression of both the polyhydroxyalkanoate biosynthetic pathway and the succinic semialdehyde metabolic pathway within the host cell, to produce the polyhydroxyalkanoate.

2. The process of claim 1 wherein the recombinant nucleotide sequences are contained on one or more vector constructs.

3. The process of claim 1 wherein the method further comprises the step of isolating the polyhydroxyalkanoate from the host cell.

4. The process of claim 1 wherein the at least one sequence recombinant nucleotide encoding the succinic semialdehyde metabolic pathway further comprises a sequence recombinant nucleotide encoding a succinic semialdehyde dehydrogenase.

5. The process of claim 4 wherein the succinic semialdehyde dehydrogenase is able to convert succinyl-CoA to succinic semialdehyde.

6. The process of claim 1 wherein the at least one sequence recombinant nucleotide encoding the succinic semialdehyde metabolic pathway further comprises a sequence recombinant nucleotide encoding a succinyl-CoA:CoA transferase.

7. The process of any one of claims 1–6 wherein the polyhydroxyalkanoate biosynthetic pathway is encoded by a single sequence recombinant nucleotide contained in a first vector construct, and the succinic semialdehyde metabolic pathway is encoded by a single sequence recombinant nucleotide contained in a second vector construct.

8. The process of any one of claims 1–6 wherein the polyhydroxyalkanoate biosynthetic pathway and the succinic semialdehyde metabolic pathway are encoded by sequences recombinant nucleotide contained in a single vector construct.

9. The process of any one of claims 1–6 wherein the succinic semialdehyde metabolic pathway is from *Clostridium kluyveri*.

10. The process of any one of claims 1–6 wherein the polyhydroxyalkanoate biosynthetic pathway is from *Ralstonia eutropha*.

11. The process of any one of claims 1–6 wherein the polyhydroxyalkanoate biosynthetic pathway comprises a polyhydroxyalkanoate synthase from *Nocardia corallina*.

12. The process of any one of claims 1–6 wherein the host cell is an *Escherichia coli* host cell.

13. The process of any one of claims 1–6 wherein the host cell is a Klebsiella host cell.

14. The process of claim 13 wherein the host cell is a *Klebsiella aerogenes* or *Klebsiella oxytoca*.

15. The process of any one of claims 1–6 wherein the host cell is a plant host cell.

16. The process of any one of claims 1–6 wherein the host cell is an insect host cell.

17. The process of any one of claims 1–6 wherein the host cell is a spider host cell.

18. The process of any one of claims 1–6 wherein the host cell has an inhibiting mutation in its CoA-independent NAD-dependent succinic independent semialdehyde dehydrogenase.

19. The process of any one of claims 1–6 wherein the host cell has an inhibiting mutation in its CoA-independent NADP-dependent succinic semialdehyde dehydrogenase.

20. The process of any one of claims 1–6 wherein the host cell has an inhibiting mutation in its CoA-independent NAD-dependent succinic independent semialdehyde dehydrogenase and its CoA-independent NADP-dependent succinic semialdehyde dehydrogenase.

21. The process of any one of claims 1–6 wherein the step of cultivating comprises cultivating the host cell on a carbon source that does not comprise 4-hydroxybutyrate or a structurally related precursor of 4-hydroxybutyrate.

22. The process of claim 21 wherein the structurally related precursor is 1,4-butanediol or 4-butyrolactone.

23. The process of any one of claims 1–6 wherein the step of cultivating comprises cultivating the host cell on a carbon source comprising a sugar having a 5-carbon or 6-carbon ring.

24. The process of any one of claims 1–6 wherein the step of cultivating comprises cultivating the host cell on a carbon source consisting essentially of glucose.

25. The process of any one of claims 1–6 wherein the step of cultivating comprises cultivating the host cell on a carbon source consisting essentially of sucrose.

26. A process for producing polyhydroxyalkanoate comprising 4-hydroxybutyrate monomer units, the method comprising:
   providing a host cell able to synthesize poly-β-hydroxyalkanoate via a polyhydroxyalkanoate biosynthetic pathway, the host cell containing at least one recombinant nucleotide sequence that encodes a succinic semialdehyde metabolic pathway that metabolizes succinic semialdehyde via a 4-hydroxybutyryl-CoA intermediate; and,
   cultivating the host cell under suitable conditions to obtain expression of the poly-β-hydroxyalkanoate pathway and the succinic semialdehyde metabolic pathway in the host cell, to produce the polyhydroxalkanoate.

27. The process of claim 26 wherein the method further comprises the step of isolating the polyhydroxalkanoate from the host cell.

28. The process of claim 26 or 27 wherein the at least one recombinant nucleotide sequence encoding the succinic semialdehyde metabolic pathway is contained on one or more vector constructs.

29. The process of claim 26 or 27 wherein the at least one sequence recombinant nucleotide encoding the succinic semialdehyde metabolic pathway further comprises a sequence recombinant nucleotide encoding a succinic semialdehyde dehydrogenase.

30. The process of claim 29 wherein the succinic semialdehyde dehydrogenase is able to convert succinyl-CoA to succinic semialdehyde.

31. The process of claim 26 or 27 wherein the at least one sequence recombinant nucleotide encoding the succinic semialdehyde metabolic pathway further comprises a sequence recombinant nucleotide encoding a succinyl-CoA:CoA transferase.

32. The process of claim 26 or 27 wherein the step of cultivating comprises cultivating the host cell on a carbon source that does not comprise 4-hydroxybutyrate or a structurally related precursor of 4-hydroxybutyrate.

33. The process of claim 32 wherein the structurally related precursor is 1,4-butanediol or 4-butyrolactone.

34. The process of claim 26 or 27 wherein the step of cultivating comprises cultivating the host cell on a carbon source consisting essentially of glucose, sucrose, fructose or lactose.

35. The process of claim 26 or 27 wherein the host cell is an *Ralstonia eutropha* host cell.

36. The process of claim 26 or 27 wherein the host cell is a *Nocardia corallina* host cell.

37. A process for producing a polyhydroxyalkanoate comprising 4-hydroxybutyrate monomer units, the method comprising:
   providing a host cell that metabolizes succinic semialdehyde via a succinic semialdehyde metabolic pathway that uses a 4-hydroxybutyryl-CoA intermediate, the host cell containing at least one recombinant nucleotide sequence that encodes a polyhydroxyalkanoate biosynthetic pathway;
   cultivating the host cell under suitable conditions to obtain expression of the succinic semialdehyde metabolic pathway and the polyhydroxyalkanoate biosynthetic pathway in the host cell, to produce the polyhydroxyalkanoate.

38. The process of claim 37 wherein the method further comprises the step of isolating the polyhydroxyalkanoate from the host cell.

39. The process of claim 37 or 38 wherein the at least one recombinant nucleotide sequence encoding the polyhydroxyalkanoate biosynthetic pathway is contained on one or more vector constructs.

40. The process of claim 37 or 38 wherein the at least one sequence recombinant nucleotide encoding the succinic semialdehyde metabolic pathway further comprises a sequence recombinant nucleotide encoding a succinic semialdehyde dehydrogenase.

41. The process of claim 26, 27 or 40 wherein the succinic semialdehyde dehydrogenase is able to convert succinyl-CoA to succinic semialdehyde.

42. The process of claim 37 or 38 wherein the at least one sequence recombinant nucleotide encoding the succinic semialdehyde metabolic pathway further comprises a sequence recombinant nucleotide encoding a succinyl-CoA:CoA transferase.

43. The process of claim 37 or 38 wherein the step of cultivating comprises cultivating the host cell on a carbon source that does not comprise 4-hydroxybutyrate or a structurally related precursor of 4-hydroxybutyrate.

44. The process of claim 43 wherein the structurally related precursor is 1,4-butanediol or 4-butyrolactone.

45. The process of claim 37 or 38 wherein the step of cultivating comprises cultivating the host cell on a carbon source consisting essentially of glucose, sucrose, fructose or lactose.

46. The process of claim 37 or 38 wherein the host cell is a *Clostridium kluyveri* host cell.

47. The process of any one of claims 1, 26 or 37 wherein the polyhydroxyalkanoate is poly(4-hydroxybutyrate) and wherein the polyhydroxyalkanoate biosynthetic pathway consists of a polyhydroxyalkanoate synthase.

48. A host cell containing at least one recombinant nucleotide sequence that encodes a polyhydroxyalkanoate biosynthetic pathway, and at least one recombinant nucleotide sequence that encodes a succinic semialdehyde metabolic pathway that metabolizes succinic semialdehyde via a 4-hydroxybutyryl-CoA intermediate.

49. The host cell of claim 48 wherein at least one of the recombinant nucleotide sequences is contained in a vector construct that expresses the sequence.

50. The host cell of claim 48 or 49 wherein the polyhydroxyalkanoate biosynthetic pathway is encoded by a single sequence recombinant nucleotide contained in a first vector construct, and the succinic semialdehyde metabolic pathway is encoded by a single sequence recombinant nucleotide contained in a second vector construct.

51. The host cell of claim 48 or 49 wherein the polyhydroxyalkanoate biosynthetic pathway and the succinic semialdehyde metabolic pathway are encoded by sequences recombinant nucleotide contained on a single vector construct.

52. The host cell of claim 48 or 49 wherein the at least one sequence recombinant nucleotide encoding the succinic semialdehyde metabolic pathway further comprises a sequence recombinant nucleotide encoding a succinic semialdehyde dehydrogenase.

53. The host cell of claim 48 or 49 wherein the succinic semialdehyde dehydrogenase is able to convert succinyl-CoA to succinic semialdehyde.

54. The host cell of claim 53 wherein the at least one sequence recombinant nucleotide encoding the succinic semialdehyde metabolic pathway further comprises a sequence recombinant nucleotide encoding a succinyl-CoA:CoA transferase.

55. The host cell of claim 48 or 49 wherein the host cell is an *Escherichia coli* host cell.

56. The host cell of claim 48 or 49 wherein the host cell is a Klebsiella host cell.

57. The host cell of claim 56 wherein the host cell is a *Klebsiella aerogenes* or *Klebsiella oxytoca*.

58. The host cell of claim 48 or 49 wherein the host cell is a plant host cell.

59. The host cell of claim 48 or 49 wherein the host cell is an insect host cell.

60. The host cell of claim 48 or 49 wherein the host cell is a spider host cell.

61. The host cell of claim 48 or 49 wherein the host cell has an inhibiting mutation in its CoA-independent NAD-dependent succinic independent semialdehyde dehydrogenase.

62. The host cell of claim 48 or 49 wherein the host cell has an inhibiting mutation in its CoA-independent NADP-dependent succinic semialdehyde dehydrogenase.

63. The host cell of claim 48 or 49 wherein the host cell has an inhibiting mutation in its CoA-independent NAD-dependent succinic independent semialdehyde dehydrogenase and its CoA-independent NADP-dependent succinic semialdehyde dehydrogenase.

64. A vector construct that expresses at least one sequence recombinant nucleotide that encodes a polyhydroxyalkanoate biosynthetic pathway, and at least one sequence recombinant nucleotide that encodes a succinic semialdehyde metabolic pathway.

65. The vector construct of claim 64 wherein the at least one sequence recombinant nucleotide encoding the succinic semialdehyde metabolic pathway further comprises a sequence recombinant nucleotide encoding a succinic semialdehyde dehydrogenase.

66. The vector construct of claim 65 wherein the succinic semialdehyde dehydrogenase is able to convert succinyl-CoA to succinic semialdehyde.

67. The vector construct of claim 64 wherein the at least one sequence recombinant nucleotide encoding the succinic semialdehyde metabolic pathway further comprises a sequence recombinant nucleotide encoding a succinyl-CoA:CoA transferase.

\* \* \* \* \*

UNITED STATES PATENT AND TRADEMARK OFFICE
CERTIFICATE OF CORRECTION

PATENT NO. : 6,117,658
DATED : September 12, 2000
INVENTOR(S) : Douglas E. Dennis and Henry E. Valentin It is certified that error appears in the above-identified patent and that said Letters Patent is hereby corrected as shown below:

Column 26, claim 4,
Lines 45 and 47, "sequence recombinant nucleotide" should read -- recombinant nucleotide sequence --.

Column 26, claim 6,
Lines 53 and 55, "sequence recombinant nucleotide" should read -- recombinant nucleotide sequence --.

Column 28, claim 37,
Lines 38 and 39, "one recombinant nucleotide sequence" should read -- one recombinant sequence --.

Column 29, claim 50,
Lines 26 and 28, "sequence recombinant nucleotide" should read -- recombinant nucleotide sequence --.

Column 29, claim 51,
Lines 32 and 33, "sequence recombinant nucleotide" should read -- recombinant nucleotide sequence --.

Column 29, claim 52,
Lines 36 and 38, "sequence recombinant nucleotide" should read -- recombinant nucleotide sequence --.

Column 29, claim 54,
Line 44, "sequence recombinant nucleotide" should read -- recombinant nucleotide sequence --.

Column 30, claim 54,
Line 1, "sequence recombinant nucleotide" should read -- recombinant nucleotide sequence --.

Column 30, claim 64,
Lines 26 and 27, "sequence recombinant nucleotide" should read -- recombinant nucleotide sequence --.
Lines 28 and 29, "sequence recombinant nucleotide" should read -- recombinant nucleotide sequence --.

UNITED STATES PATENT AND TRADEMARK OFFICE
CERTIFICATE OF CORRECTION

PATENT NO. : 6,117,658
DATED : September 12, 2000
INVENTOR(S) : Douglas E. Dennis and Henry E. Valentin It is certified that error appears in the above-identified patent and that said Letters Patent is hereby corrected as shown below:

Column 30, claim 65,
Lines 32 and 34, "sequence recombinant nucleotide" should read -- recombinant nucleotide sequence --.

Column 30, claim 67,
Lines 40 and 42, "sequence recombinant nucleotide" should read -- recombinant nucleotide sequence --.

Signed and Sealed this

Sixteenth Day of April, 2002

Attest:

JAMES E. ROGAN
Director of the United States Patent and Trademark Office

Attesting Officer